(12) United States Patent
Hedstrom et al.

(10) Patent No.: US 9,765,019 B2
(45) Date of Patent: Sep. 19, 2017

(54) SMALL-MOLECULE-TARGETED PROTEIN DEGRADATION

(75) Inventors: Lizbeth K. Hedstrom, Newton, MA (US); Marcus Long, Somerville, MA (US); Deviprasad R. Gollapalli, Waltham, MA (US)

(73) Assignee: Brandeis University, Waltham, MA (US)

( * ) Notice: Subject to any disclaimer, the term of this patent is extended or adjusted under 35 U.S.C. 154(b) by 167 days.

(21) Appl. No.: 13/805,508

(22) PCT Filed: Jun. 30, 2011

(86) PCT No.: PCT/US2011/042535
§ 371 (c)(1),
(2), (4) Date: Feb. 22, 2013

(87) PCT Pub. No.: WO2012/003281
PCT Pub. Date: Jan. 5, 2012

(65) Prior Publication Data
US 2013/0190340 A1  Jul. 25, 2013

(51) Int. Cl.
| | | |
|---|---|---|
| *A01N 43/54* | (2006.01) | |
| *C07D 239/42* | (2006.01) | |
| *C07D 401/04* | (2006.01) | |
| *C07C 279/14* | (2006.01) | |
| *A61K 31/4184* | (2006.01) | |
| *A61K 31/505* | (2006.01) | |
| *C07C 65/40* | (2006.01) | |
| *C07C 211/12* | (2006.01) | |
| *C07D 239/49* | (2006.01) | |
| *C07D 271/12* | (2006.01) | |
| *A61K 47/48* | (2006.01) | |

(52) U.S. Cl.
CPC ........ *C07C 279/14* (2013.01); *A61K 31/4184* (2013.01); *A61K 31/505* (2013.01); *A61K 47/48023* (2013.01); *A61K 47/48038* (2013.01); *A61K 47/48061* (2013.01); *C07C 65/40* (2013.01); *C07C 211/12* (2013.01); *C07D 239/49* (2013.01); *C07D 271/12* (2013.01)

(58) Field of Classification Search
None
See application file for complete search history.

(56) References Cited

U.S. PATENT DOCUMENTS

| | | |
|---|---|---|
| 5,851,791 A | 12/1998 | Vierstra et al. |
| 6,217,864 B1 | 4/2001 | Coffino et al. |
| 2005/0152888 A1 | 7/2005 | Church et al. |
| 2007/0059376 A1 | 3/2007 | Takeoka et al. |
| 2010/0047179 A1 | 2/2010 | Demidov et al. |
| 2010/0087474 A1 | 4/2010 | Kaushal et al. |

FOREIGN PATENT DOCUMENTS

| | | |
|---|---|---|
| WO | WO-98/51702 | 11/1998 |
| WO | WO-02/36075 | 5/2002 |

OTHER PUBLICATIONS

Pozdnev, "Na,NG,NG-Tri-tert-butyloxycarbonylarginine. A new arginine derivative for peptide synthesis", Bioorganicheskaya Khimiya, 1986, vol. 12, No. 8, pp. 1013-1022; Abstract.*
Neidle, Cancer Drug Design and Discovery, Elsevier/Academic Press, 2008, pp. 427-431.*
International Search Report dated Apr. 6, 2012, from PCT/US2011/042535.
Hidvegi et al., "An Autophagy-Enhancing Drug Promotes Degradation of Mutant $\alpha_1$-Antitrypsin Z and Reduces Hepatic Fibrosis," Science, 329:229-232 (2010).
Long et al., "Inhibitor Mediated Protein Degradation," Chemistry & Biology, 19(5):629-637 (2012).
Mehrpour et al., "Drug enhanced autophagy to fight mutuant protein overload," Journal of Hepatology, 54(5):1066-1068 (2011).
Neklesa et al., "Small-Molecule Hydrophobic Tagging Induced Degradation of HaloTag Fusion Proteins," Nature Chemical Biology, 7(8):538-543 (2011).
Sarkar et al., "Small molecules enhance autophagy and reduce toxicity in Huntington's disease models," Nature Chemical Biology, 3(6):331-338 (2007).
Tae et al., "Identification of Hydrophobic Tags for the Degradation of Stablized Proteins," Chembiochem, 13(4):538-541 (2012).
Wu et al., "Targeted Ubiquitination and Degradation of G-Protein-Coupled Receptor Kinase 5 by the DDB1-CUL4 Ubiquitin Ligase Complex," PLOS One, 7(8):e43997 (2012).
Supplementary European Search Report dated Jun. 5, 2014 from EP 11 80 1391.

* cited by examiner

*Primary Examiner* — Jeffrey S Lundgren
*Assistant Examiner* — Stephanie Springer
(74) *Attorney, Agent, or Firm* — Foley Hoag LLP

(57) ABSTRACT

Certain aspects of the invention relate to compounds, compositions and methods that are useful for treating or preventing a disease in a subject by enhancing the degradation of a protein. In other aspects, said compounds can be useful research tools for investigating protein degradation. In other aspects, said compounds are useful research tools for investigating protein function. In certain embodiments, the degraded protein is implicated in a disease or disorder whose pathology is related at least in part to the excessive expression of the protein or the expression of a mutant form of the protein.

12 Claims, 15 Drawing Sheets

Figure 2
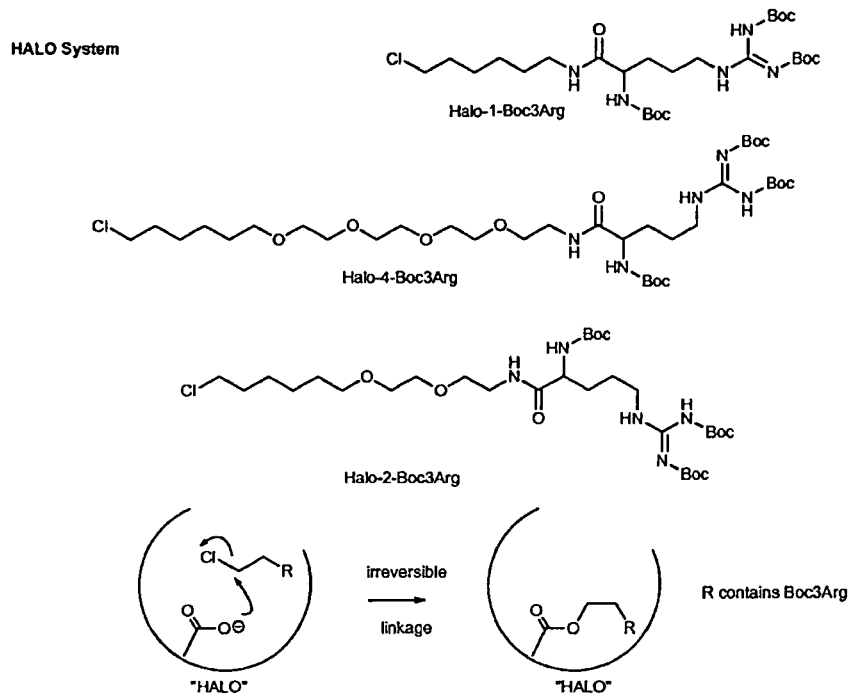
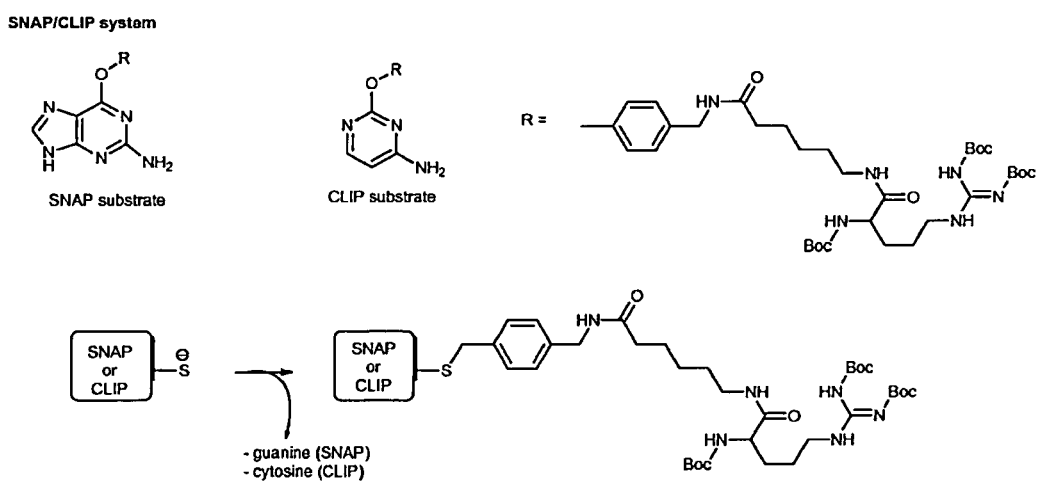

Figure 9
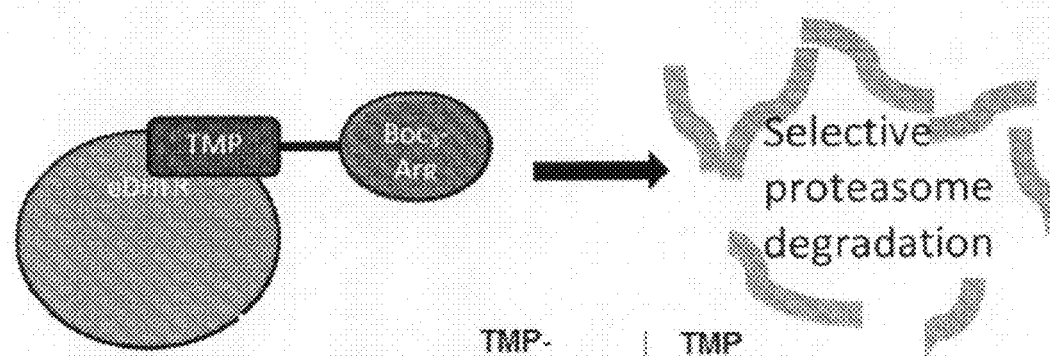
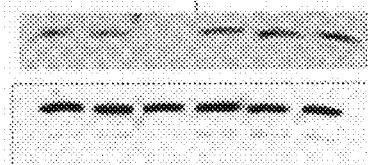

| Cmpd | R1 | R3 | pK$_i$ |
|---|---|---|---|
| TMP | OCH$_3$ | OCH$_3$ | 8.87 |
| T1 | OCH$_3$ | OCH$_3$ | 8.35 |
| T2 | CF$_3$ | H | 7.69 |
| T3 | H | H | 6.89 |
| T4 | CH$_2$CH$_3$ | CH$_2$CH$_3$ | 5.75 |

Pthalimide derivative

SMALL-MOLECULE-TARGETED PROTEIN DEGRADATION

GOVERNMENT SUPPORT

This invention was made with U.S. Government support under Grant Nos. ROI GM054403 and U01 A1075466 awarded by the National Institutes of Health. The government has certain rights in the invention.

This application is the U.S. National Stage of International Patent Application No. PCT/US11/042535, filed Jun. 30, 2011, which claims the benefit of priority to U.S. Provisional Patent Application Ser. No. 61/360,257, filed Jun. 30, 2010.

RELATED APPLICATIONS

This application claims the benefit of priority to U.S. Provisional Patent Application Ser. No. 61/360,257, filed Jun. 30, 2010, the contents of which are hereby incorporated by reference.

BACKGROUND

A formidable toolkit exists for manipulating protein expression at the transcriptional level, but the methods for post-translational modulation are few and largely rely on the expression of fusion proteins. While such systems can provide important insights into cellular processes, the necessity of fusion protein expression can be constraining and the potential for therapeutic use is nil. A small molecule strategy to induce the degradation of endogenous proteins would clearly be a tremendously useful tool for probing protein function and an exciting new approach for chemotherapy. The challenge is to develop technology that is widely applicable.

Targeted gene knockout and RNAi are currently the methods choice for removing endogenous proteins. Both methods have been enormously useful, but both have serious limitations. The proteins of greatest interest are often essential and therefore not amenable to gene knockout. While this problem can often be circumvented with regulated gene expression or conditional gene targeting (e.g., the tetracycline and Cre-loxP systems), such experiments can be difficult to interpret because of the long time between loss of gene expression and protein depletion. RNAi is also limited by the time of induction, which can be many days. RNAi knockdown can often be incomplete or beset with off-target effects. Importantly, not all organisms have RNAi pathways: it is notably absent in the malaria parasite. More seriously, major hurdles in permeability and delivery will need to be surmounted before this method can have widespread use in mammals and in the clinic. These issues might be avoided if the intracellular protein degradation machinery could be exploited via a small molecule.

Several laboratories have developed systems where small molecules regulate protein degradation. The most common strategy involves expression of fusion proteins that couple the target to an unstable "degron" domain. The degron domain is stabilized by the presence of a ligand; removal of the ligand induces degradation. For example, unstable DHFR mutants have been used to create a temperature sensitive degron that is stabilized by methotrexate or trimethoprim (TMP). Other systems use degrons based on the rapamycin interacting proteins FKBP12 and FKBP-rapamycin binding protein (FRB). These domains are unstable in the absence of rapamycin-based ligands; again degradation is induced when the ligand is removed. A particularly clever use of the rapamycin-based dimerization is found in the SURF system. In this case, rapamycin stops degradation by causing the degron to be removed from the target protein. These systems have proven very useful, but are limited by the requirement for the constant presence of ligand to maintain protein levels—a system that induced degradation by addition of a small molecule would be easier to maintain. Another approach uses a pair of fusion proteins to localize a target protein directly to the proteasome, with one partner on the target protein and a second on a proteasome subunit. Importantly, the success of this strategy demonstrates that proteasome localization is sufficient to induce degradation. A similar strategy has been used to target protein degradation in bacteria. The systems described above modulate levels of transgenic fusion proteins with varying degrees of success, but cannot be used to reduce the levels of endogenous proteins.

Proteolysis targeting chimeric molecules (PROTACs) have been described. PROTACs contain a ligand that recognizes the target protein linked to a ligand that binds to a specific E3 ubiquitin ligase. Degradation of methionine aminopeptidase, androgen receptor, estrogen receptor and the aryl hydrocarbon receptor have been reported. In most cases, the E3 ligase-targeting ligand is a peptide, which limits therapeutic use. In addition, this method will only work in cells and organisms that express the targeted E3 ligase. More generally, the ubiquitin pathways are extremely complicated and poorly understood, which suggests that controlled manipulation of these pathways difficult. A small molecule strategy that targets proteins directly to the proteasome would have many advantages over PROTACs.

Additionally, proteins must fold into their correct three-dimensional conformation to achieve their biological function. The native conformation of a polypeptide is encoded within its primary amino acid sequence, and even a single mutation in an amino acid sequence can impair the ability of a protein to achieve its proper conformation and/or function. When proteins fail to fold correctly, or are not active, the biological and clinical effects can be devastating. For example, protein aggregation and misfolding are primary contributors to many human diseases, such as autosomal dominant retinitis pigmentosa, Alzheimer's disease, α1-antitrypsin deficiency, cystic fibrosis, nephrogenic diabetes insipidus, and prion-mediated infections. In other protein-folding disorders, such as age-related macular degeneration, Parkinson's disease, and Huntington's disease, pathology results because of the cytotoxic effects of the misfolded protein.

Mutant (e.g., misfolded) proteins are often recognized by the endoplasmic reticulum (ER) quality control system and targeted for degradation by the proteasome. Besides the proteasomal pathway, autophagy is another major cellular mechanism for protein degradation. While autophagy can be stimulated by a variety of intracellular and extracellular stresses, including amino-acid starvation, aggregation of protein, and accumulation of damaged organelles, autophagy appears to be a largely non-selective process. Aggregate-prone polyglutamine and polyalanine expanded proteins associated with Huntington's disease are degraded by autophagy, and inhibition of autophagy reduces the toxicity of mutant Huntington proteins in fly and mouse models of Huntington disease. Autophagy has also been shown to contribute to the elimination of proteins accumulated in the ER. Methods for increasing the degradation of mutated proteins might enhance the elimination of such proteins, thereby decreasing or eliminating their cytotoxic effects. See, for example, United States Patent Application No. 2010/0087474 A1 entitled "Materials and Methods for Enhanced Degradation of Mutant Proteins Associate with Human Disease," which is hereby incorporated by reference in its entirety. A small molecule strategy to induce the degradation of mutant proteins would also be a useful tool.

SUMMARY

Certain aspects of the invention relate to compounds comprising a protein-binding moiety which binds a protein, a tag which promotes the degradation of said protein (a recognition element), and a covalent linker which connects the protein-binding moiety to the tag. In certain embodiments the invention also relates to the use of said compounds for modulating the level and/or activity of a target protein. In certain embodiments the invention relate to compounds, compositions and methods that are useful for treating or preventing a disease in a subject by enhancing the degradation of proteins in vivo. In certain embodiments, said compounds can be useful research tools for investigating protein degradation. In certain embodiments, the degraded protein is implicated in a disease or disorder whose pathology is related at least in part to the excessive expression of the protein or the expression of a mutant form of the protein. In certain embodiments, the compounds, compositions and methods are useful for the treatment of disease such as infections, inflammatory conditions, diabetes, cardiovascular disease, cancer and genetic diseases. In other embodiments, the compounds, compositions and methods are also useful as insecticides and herbicides. Additional aspects, embodiments, and advantages of the invention are discussed below in detail.

BRIEF DESCRIPTION OF THE FIGURES

FIG. 2 depicts examples of compounds of the invention, and their use with fusion proteins. In this case, the HALO, SNAP, or CLIP protein is part of a fusion protein further comprising the protein to be degraded.

FIG. 9 depicts a schematic representation of the ligand-mediated protein degradation of the invention.

DETAILED DESCRIPTION

Overview

Certain aspects of the invention relate to compositions and methods that are useful for selectively enhancing the degradation of proteins in vivo. In certain embodiments, the invention is based on the discovery that compounds of the invention can be used to target specific proteins and enhance their degradation. Advantageously, in certain embodiments, mutated proteins can be selectively degraded, while levels of the respective wild-type forms remain largely unchanged.

The therapeutic potential of such agents is easily seen in cancer chemotherapy, but also widely applicable to other diseases. Oncoprotein degradation is an emerging strategy in cancer chemotherapy. The improved action of fulvestrant over tamoxifen in the treatment of breast cancer is attributed to its ability to induce degradation of the estrogen receptor. Importantly, tamoxifen-resistant breast cancer cells remain sensitive to selective estrogen receptor down-regulators (SERDS), illustrating the therapeutic potential of this strategy. Other SERDs are currently in development. Similar degradation of the androgen receptor is observed with casodex treatment. Likewise, the success of the retinoic acid/arsenic trioxide combination in acute promyelocytic leukemia (APL) therapy results from its ability to induce the degradation of the oncogenic fusion protein PML-RARA. It is clear that simply blocking the kinase activity of the Bcr-Abl kinase is not sufficient to block activation of its downstream signaling pathways; obviously such kinase-independent signaling would be eliminated if Bcr-Abl was degraded. The degradation of aberrant proteins would also provide a novel and much-needed strategy for treating hereditary diseases. For example, mutations in IMPDH1 cause retinitis pigmentosa, an inherited blindness resulting from the degeneration of rod photoreceptors. IMPDH1 knockout mice display only a mild retinopathy, suggesting that the removal of the mutant protein will prevent disease. Treatment of botulinum toxin (BoNT) intoxication highlights another advantage of this strategy. BoNT has a half-life of 90 days, so patients must be kept on respirators for many months; a small molecule inhibitor of BoNT would also have to be administered for many months, but an agent that could induce the degradation of BoNT would require a much reduced treatment schedule. More generally, it has recently been recognized that inhibitors with long residence times on their targets are more efficacious in vivo. This observation has led to the idea that a perfect drug irreversibly inactivates its target, so that only new synthesis of the target protein restores activity. Obviously, a drug that induced degradation is perfect by this definition. These examples show that a generally applicable strategy for the design of small molecules that can induce protein degradation would be a major advance with broad impact.

Figure 1:
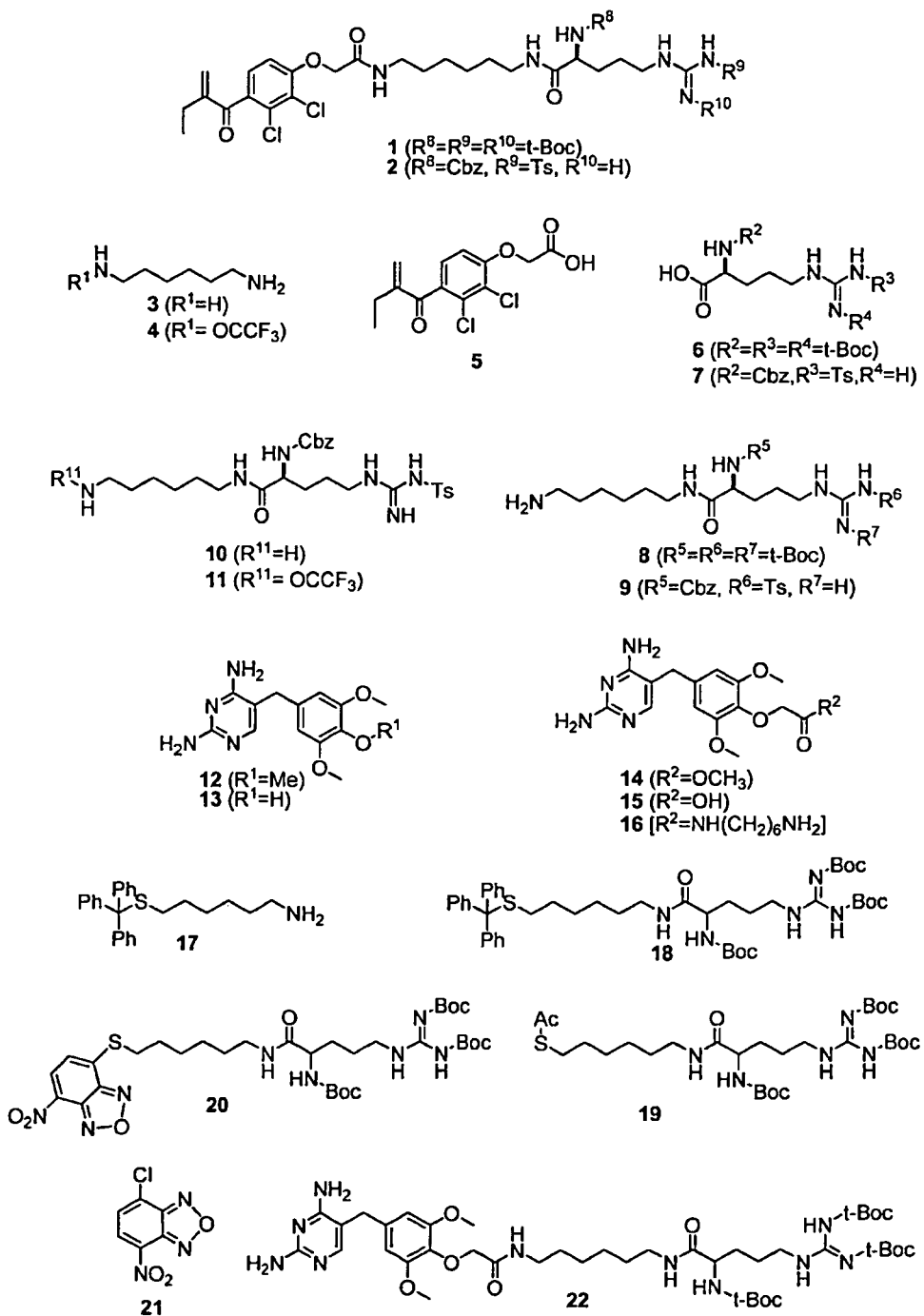
FIG. 1 depicts examples of compounds of the invention.

In certain embodiments, the compounds of the invention comprise a protein-binding moiety which binds a protein, a tag which promotes the degradation of said protein, and a covalent linker which connects the protein-binding moiety to the tag. In certain embodiments, the protein-binding moiety is an inhibitor of human glutathione-S-transferase α1 (GST) or an inhibitor of *Escherichia coli* dihydrofolate reductase (DHFR). In certain embodiments, the protein-binding moiety is a modifier of $O^6$-alkylguanine-DNA alkyltransferase (SNAP), a modifier of the CLIP variant of SNAP, or a modifier of engineered haloalkane dehalogenase (HALO). Specifically, in certain embodiments, the protein-binding moiety is derived from ethacrynic acid (an inhibitor of GST), thiobenzofuran (an inhibitor of GST), or trimethoprim (an inhibitor of bacterial DHFR), as shown in FIG. 1. Specifically, in certain embodiments, the protein-binding moiety is derived from $O^6$-alkylguanine (a modifier of SNAP), $O^2$-benzylcytosine (a modifier of CLIP), or alkylchloride (a modifier of HALO). In certain embodiments, the tags comprise oxidized amino acids, lipid oxidative degradation products or N-end rule residues. In certain embodiments, the tags comprise a modified arginine.

In certain embodiments, modified inhibitors were assayed for the ability to cause degradation of their target proteins both in vitro using mammalian cell lysates derived from Cos, HeLa and NIH 3T3 cells; and in vivo using transiently transfected Cos and HeLa cells. Remarkably, it was discovered that a modified arginine tag promotes the degradation of both target proteins in cell lysate assays (1 and 22), in whole cell assays (22), and using purified 20S and immune proteasome (22). In addition, it was discovered that tosyl arginine derivative 2 is a functional degradation tag in cell lysate assays.

In certain embodiments, compounds of the invention should be useful in treating a variety of diseases that are due at least in part to excessive protein expression or expression of a mutant protein. For example, compounds of the invention should be useful in treating intoxication with botulinum toxin (BoNT). The half life of BoNT is about ninety days in motor neurons. A strategy to decrease the titer of BoNT would be an effective alternative to conventional small molecule inhibitor therapy, which typically requires a long course of treatment. Another potential application is in treating inherited diseases where the presence of a mutant protein contributes to or causes pathology. For example, IMP dehydrogenase type 1 (IMPDH1)-mediated retinitis pigmentosa is an inherited retinopathy caused by mutations in IMPDH1 that do not affect enzymatic activity. IMPDH1 (−/−) mice do not display similar visual defects, suggesting that the presence of the mutant protein is more damaging than the absence of IMPDH1. Therefore, removal of the mutant protein via degradation should be an effective therapeutic strategy. For example, chronic myelogenous leukemia is caused by expression of the Bcr-Abl protein kinase. Inhibition of the kinase activity is not sufficient to block all Bcr-Abl signaling. Such inhibitor-independent signaling would be eliminated if Bcr-Abl were degraded.

Definitions

For convenience, certain terms employed in the specification, examples, and appended claims are collected here. All definitions, as defined and used herein, supersede dictionary definitions, definitions in documents incorporated by reference, and/or ordinary meanings of the defined terms.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising"

can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "solvate" refers to a pharmaceutically acceptable form of a specified compound, with one or more solvent molecules, that retains the biological effectiveness of such compound. Examples of solvates include compounds of the invention in combination with solvents such as, for example, water (to form the hydrate), isopropanol, ethanol, methanol, dimethyl sulfoxide, ethyl acetate, acetic acid, ethanolamine, or acetone. Also included are formulations of solvate mixtures such as a compound of the invention in combination with two or more solvents.

The definition of each expression, e.g., alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., a compound which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "lower" when appended to any of the groups listed below indicates that the group contains less than seven carbons (i.e., six carbons or less). For example "lower alkyl" refers to an alkyl group containing 1-6 carbons, and "lower alkenyl" refers to an alkyenyl group containing 2-6 carbons.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged). "Monocyclic" refers to compounds and/or groups with one ring; and "bicyclic" refers to compounds/and or groups with two rings.

The term "aromatic" refers to a planar or polycyclic structure characterized by a cyclically conjugated molecular moiety containing $4n+2$ electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "hydrocarbon" as used herein refers to an organic compound consisting entirely of hydrogen and carbon.

For purposes of this invention, the chemical elements are identified in accordance with the Periodic Table of the Elements, CAS version, Handbook of Chemistry and Physics, 67th Ed., 1986-87, inside cover.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkyl" means an aliphatic or cyclic hydrocarbon radical containing from 1 to 20, 1 to 15, or 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, 1-(1-ethylcyclopropyl)ethyl and 1-cyclohexylethyl.

The term "cycloalkyl" is a subset of alkyl which refers to cyclic hydrocarbon radical containing from 3 to 15, 3 to 10, or 3 to 7 carbon atoms. Representative examples of cycloalkyl include, but are not limited to, cyclopropyl and cyclobutyl.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene," is art-recognized, and as used herein pertains to a diradical obtained by removing two hydrogen atoms of an alkyl group, as defined above.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "heterocyclyl", as used herein refers to a radical of a non-aromatic, ring system, including, but not limited to, monocyclic, bicyclic and tricyclic rings, which can be completely saturated or which can contain one or more units of unsaturation, for the avoidance of doubt, the degree of unsaturation does not result in an aromatic ring system, and have 3 to 12 atoms including at least one heteroatom, such as nitrogen, oxygen, or sulfur. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl, naphthyridinyl, azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluororalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluororalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxyl, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g., methylene).

The term "aryl," as used herein means a phenyl, naphthyl, phenanthrenyl, or anthracenyl group. The aryl groups of the present invention can be optionally substituted with 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluororalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluororalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxyl, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluororalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g., methylene).

The term "arylene," is art-recognized, and as used herein pertains to a diradical obtained by removing two hydrogen atoms of an aryl ring, as defined above.

The term "arylalkyl" or "aralkyl" as used herein means an aryl group, as defined herein, appended to the parent molecular moiety through an alkyl group, as defined herein. Representative examples of aralkyl include, but are not limited to, benzyl, 2-phenylethyl, 3-phenylpropyl, and 2-naphth-2-ylethyl.

The term "biaryl," as used herein means an aryl-substituted aryl, an aryl-substituted heteroaryl, a heteroaryl-substituted aryl or a heteroaryl-substituted heteroaryl, wherein aryl and heteroaryl are as defined herein. Representative examples include 4-(phenyl)phenyl and 4-(4-methoxyphenyl)pyridinyl.

The term "heteroaryl" as used herein include radicals of aromatic ring systems, including, but not limited to, monocyclic, bicyclic and tricyclic rings, which have 3 to 12 atoms including at least one heteroatom, such as nitrogen, oxygen, or sulfur. For purposes of exemplification, which should not be construed as limiting the scope of this invention: aminobenzimidazole, benzimidazole, azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluororalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluororalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxyl, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluororalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heteroaryl group through an alkylene moiety (e.g., methylene).

The term "heteroarylene," is art-recognized, and as used herein pertains to a diradical obtained by removing two hydrogen atoms of a heteroaryl ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "fused bicyclyl" as used herein means the radical of a bicyclic ring system wherein the two rings are ortho-fused, and each ring, contains a total of four, five, six or seven atoms (i.e., carbons and heteroatoms) including the two fusion atoms, and each ring can be completely saturated, can contain one or more units of unsaturation, or can be completely unsaturated (e.g., in some case, aromatic). For the avoidance of doubt, the degree of unsaturation in the fused bicyclyl does not result in an aryl or heteroaryl moiety.

The term "halo" or "halogen" means —Cl, —Br, —I or —F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

The term "fluoroalkyl" means an alkyl group, as defined herein, wherein some or all of the hydrogens are replaced with fluorines.

The term "haloalkylene," as used herein pertains to diradical obtained by removing two hydrogen atoms of an haloalkyl group, as defined above.

The term "hydroxy" as used herein means an —OH group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkyenyloxy", "alkynyloxy", "carbocyclyloxy", and "heterocyclyloxy" are likewise defined.

The term "haloalkoxy" as used herein means an alkoxy group, as defined herein, wherein at least one hydrogen is replaced with a halogen, as defined herein. Representative examples of haloalkoxy include, but are not limited to, chloromethoxy, 2-fluoroethoxy, trifluoromethoxy, and pentafluoroethoxy. The term "fluoroalkyloxy" is likewise defined.

The term "aryloxy" as used herein means an aryl group, as defined herein, appended to the parent molecular moiety through an oxygen. The term "heteroaryloxy" as used herein means a heteroaryl group, as defined herein, appended to the parent molecular moiety through an oxygen. The terms "heteroaryloxy" is likewise defined.

The term "arylalkoxy" or "arylalkyloxy" as used herein means an arylalkyl group, as defined herein, appended to the parent molecular moiety through an oxygen. The term "heteroarylalkoxy" is likewise defined. Representative examples of aryloxy and heteroarylalkoxy include, but are not limited to, 2-chlorophenylmethoxy, 3-trifluoromethylphenylethoxy, and 2,3-dimethylpyridinylmethoxy.

The term "sulfhydryl" or "thio" as used herein means a —SH group.

The term "alkylthio" as used herein means an alkyl group, as defined herein, appended to the parent molecular moiety through a sulfur. Representative examples of alkylthio include, but are not limited, methylthio, ethylthio, tert-butylthio, and hexylthio. The terms "haloalkylthio", "fluoroalkylthio", "alkyenylthio", "alkynylthio", "carbocyclylthio", and "heterocyclylthio" are likewise defined.

The term "arylthio" as used herein means an aryl group, as defined herein, appended to the parent molecular moiety through an sulfur. The term "heteroarylthio" is likewise defined.

The term "arylalkylthio" or "aralkylthio" as used herein means an arylalkyl group, as defined herein, appended to the parent molecular moiety through an sulfur. The term "heteroarylalkylthio" is likewise defined.

The term "sulfonyl" as used herein refers to —S(=O)$_2$— group.

The term "sulfonic acid" as used herein refers to —S(=O)$_2$OH.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl. The terms "haloalkylsulfonyl", "fluororalkylsulfonyl", "alkenylsulfonyl", "alkynylsulfonyl", "carbocyclylsulfonyl", "heterocyclylsulfonyl", "arylsulfonyl", "aralkylsulfonyl", "heteroarylsulfonyl" and "heteroaralkylsulfonyl" are likewise defined.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl. The terms "haloalkoxysulfonyl", "fluoroalkoxysulfonyl", "alkenyloxysulfonyl", "alkynyloxysulfonyl", "carbocyclyloxysulfonyl", "heterocyclyloxysulfonyl", "aryloxysulfonyl", "aralkyloxysulfonyl", "heteroaryloxysulfonyl" and "heteroaralkyloxysulfonyl" are likewise defined.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "aminosulfonyl" as used herein means an amino group, as defined herein, appended to the parent molecular moiety through a sulfonyl group.

The term "sulfinyl" as used herein refers to —S(=O)— group. Sulfinyl groups are as defined above for sulfonyl groups. The term "sulfinic acid" as used herein refers to —S(=O)OH.

The term "oxy" refers to a —O— group.

The term "carbonyl" as used herein means a —C(=O)— group.

The term "thiocarbonyl" as used herein means a —C(=S)— group.

The term "formyl" as used herein means a —C(=O) hydrogen group.

The term "acyl" as used herein refers to any group or radical of the form —C(=O)R, where R is an organic group. An example of the acyl group is the acetyl group (—C(=O)CH$_3$).

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl. The terms "haloalkylcarbonyl", "fluoroalkylcarbonyl", "alkenylcarbonyl", "alkynylcarbonyl", "carbocyclylcarbonyl", "heterocyclylcarbonyl", "arylcarbonyl", "aralkylcarbonyl", "heteroarylcarbonyl", and "heteroaralkylcarbonyl" are likewise defined.

The term "carboxyl" as used herein means a —CO$_2$H group.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl. The terms "haloalkoxycarbonyl", "fluoroalkoxycarbonyl", "alkenyloxycarbonyl", "alkynyloxycarbonyl", "carbocyclyloxycarbonyl", "heterocyclyloxycarbonyl", "aryloxycarbonyl", "aralkyloxycarbonyl", "heteroaryloxycarbonyl", and "heteroaralkyloxycarbonyl" are likewise defined.

The term "alkylcarbonyloxy" as used herein means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. The terms "haloalkylcarbonyloxy", "fluoroalkylcarbonyloxy", "alkenylcarbonyloxy", "alkynylcarbonyloxy", "carbocyclylcarbonyloxy", "heterocyclylcarbonyloxy", "arylcarbonyloxy", "aralkylcarbonyloxy", "heteroarylcarbonyloxy", and "heteroaralkylcarbonyloxy" are likewise defined.

The term "alkylsulfonyloxy" as used herein means an alkylsulfonyl group, as defined herein, appended to the parent molecular moiety through an oxygen atom. The terms "haloalkylsulfonyloxy", "fluoroalkylsulfonyloxy", "alkenylsulfonyloxy", "alkynylsulfonyloxy", "carbocyclylsulfonyloxy", "heterocyclylsulfonyloxy", "arylsulfonyloxy", "aralkylsulfonyloxy", "heteroarylsulfonyloxy", "heteroaralkylsulfonyloxy", "haloalkoxysulfonyloxy", "fluoroalkoxysulfonyloxy", "alkenyloxysulfonyloxy", "alkynyloxysulfonyloxy", "carbocyclyloxysulfonyloxy", "heterocyclyloxysulfonyloxy", "aryloxysulfonyloxy", "aralkyloxysulfonyloxy", "heteroaryloxysulfonyloxy" and "heteroaralkyloxysulfonyloxy" are likewise defined.

The term "amino" or "amine" as used herein refers to —NH$_2$ and substituted derivatives thereof wherein one or both of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarbonyl, heteroaralkylcarbonyl and the sulfonyl and sulfinyl groups defined above; or when both hydrogens together are replaced with an alkylene group (to form a ring which contains the nitrogen). Representative examples include, but are not limited to methylamino, acetylamino, and dimethylamino.

The term "amido" as used herein means an amino group, as defined herein, appended to the parent molecular moiety through a carbonyl.

The term "cyano" as used herein means a —C≡N group.

The term "nitro" as used herein means a —NO$_2$ group.

The term "azido" as used herein means a —N$_3$ group.

The term "phosphinyl" or "phosphino" as used herein includes —PH$_3$ and substituted derivatives thereof wherein one, two or three of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "phosphoryl" as used herein refers to —P(=O)OH$_2$ and substituted derivatives thereof wherein one or both of the hydroxyls are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "silyl" as used herein includes H$_3$Si— and substituted derivatives thereof wherein one, two or three of the hydrogens are independently replaced with substituents selected from alkyl, haloalkyl, fluoroalkyl, alkenyl, alkynyl, carbocyclyl, heterocyclyl, aryl, aralkyl, heteroaryl, and heteroaralkyl. Representative examples include trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The abbreviations Me, Et, Ph, Tf, Nf, Ts, Ms, Cbz, and Boc represent methyl, ethyl, phenyl, trifluoromethanesulfonyl, nonafluorobutanesulfonyl, p-toluenesulfonyl methanesulfonyl, carbobenzyloxy, and tert-butyloxycarbonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

By "protein-expression related disease" is meant a disease or disorder whose pathology is related at least in part to inappropriate protein expression (e.g., expression at the wrong time and/or in the wrong cell), excessive protein expression or expression of a mutant protein. In one embodiment, a mutant protein disease is caused when a mutant protein interferes with the normal biological activity of a cell, tissue, or organ.

By "mutant protein" is meant a protein having an alteration that affects its primary, secondary or tertiary structure relative to a reference (wild type) protein.

By "enhances" is meant a positive alteration of at least about 10%, 15%, 25%, 50%, 75%, or 100%.

By "reduces" is meant a negative alteration of at least about 10%, 25%, 50%, 75%, or 100%.

By "selective degradation" is meant degradation that preferentially affects a targeted protein, such that other proteins are substantially unaffected. In various embodiments, less than about 45%, 35%, 25%, 15%, 10%, or 5% of non-targeted proteins are degraded.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Boc$_3$-Arg-Mediated Degradation

Figure 5:
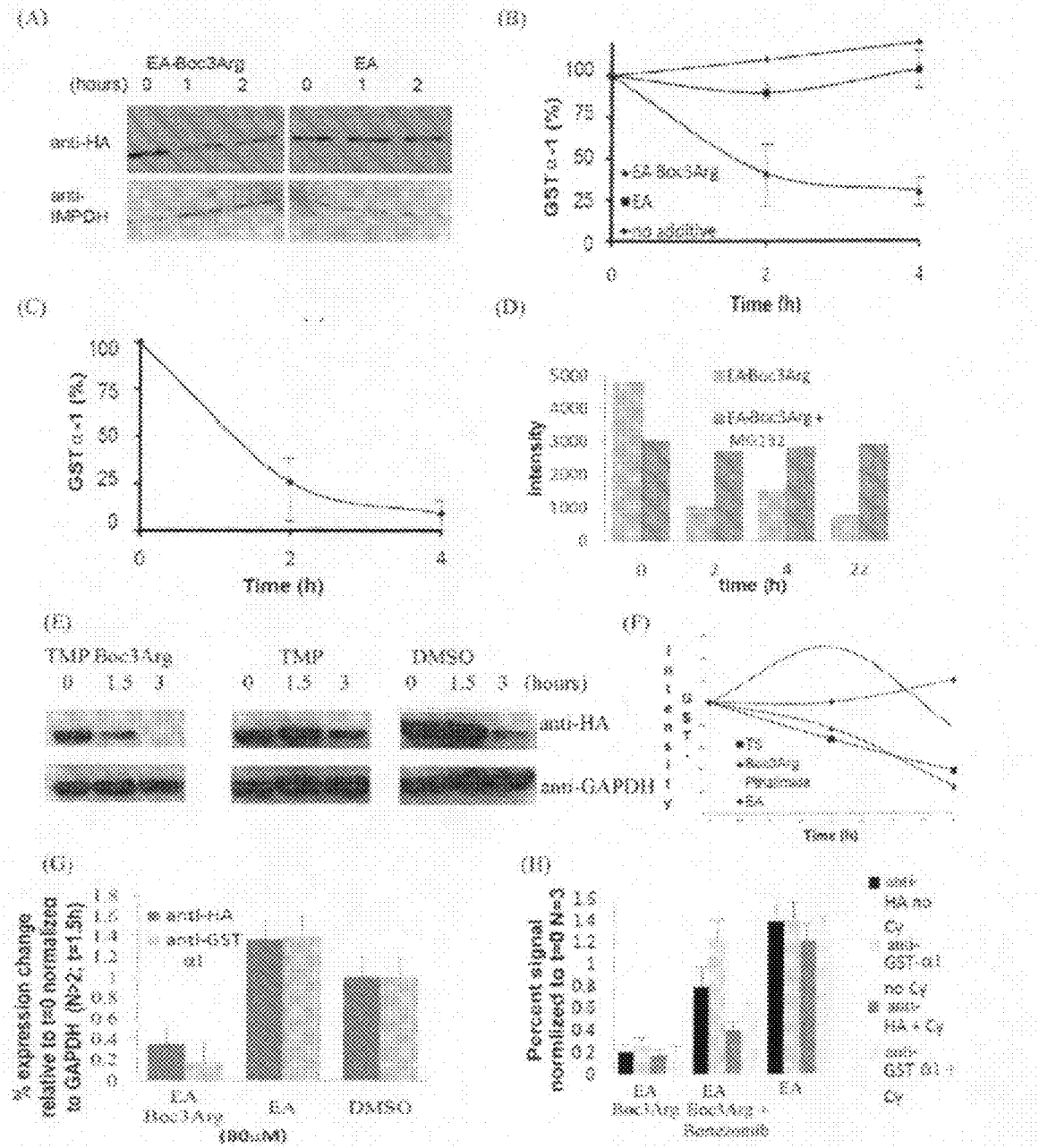
FIG. 5 depicts degradation of GST-α1-HA in HeLa cell lysates and eDHFR-HA-GST in HeLa cells. Proteasome inhibitors bortezomib (Velcade®) and MG 132 prevent degradation. (A) degradation of GST-α1-HA pretreated with EA-Boc$_3$Arg added to HeLa lysates; (B) Degradation of GST-α1-HA pretreated with EA-Boc$_3$Arg in cell lysates averaged over 3 events and quantified; (C) Degradation of GST-HA pretreated with Fur-Boc3Arg in cell lysates; (D) Effect of MG 132 on degradation of GST-HA pretreated with EA-Boc3Arg; (E) degradation of eDHFR-HA-GST-α1 ectopically expressed in HeLa cells treated with cyclohexi-mide; (F) Degradation of GST-HA pretreated with different inhibitors in HeLa cell lysates (TS=2; Boc$_3$Arg=1) (G) Treatment of cells with EA-Boc$_3$Arg can cause degradation of eDHFR-HA-GST-α1 in cycloheximide treated HeLa cells over numerous events, treatment with EA or DMSO does not; (H) Bortezomib retards degradation of eDHFR-HA-GST-α1 by EA-Boc$_3$Arg in both cycloheximide (Cy) and non-cycloheximide (no Cy) treated HeLa cells.
Figure 10:
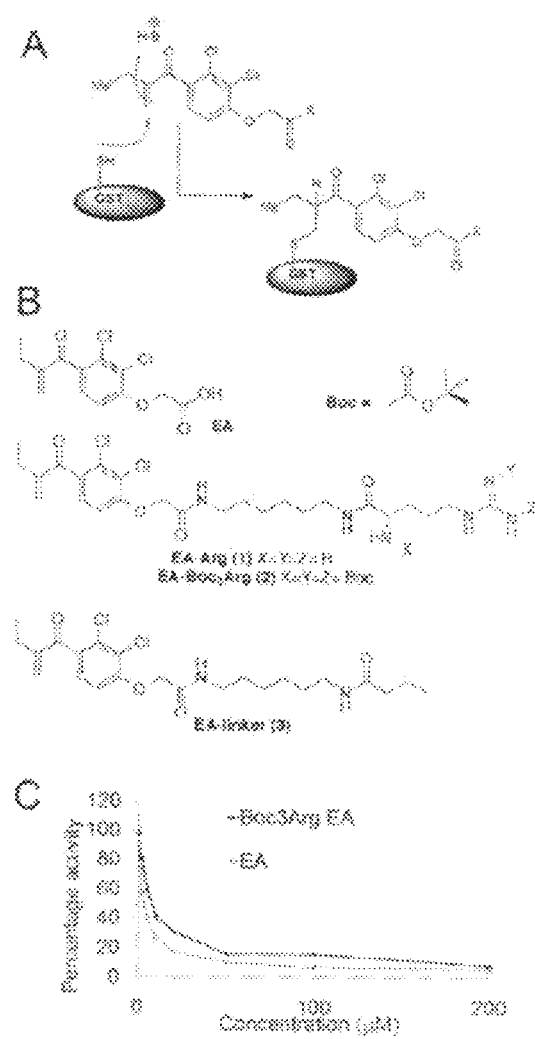
FIG. 10 depicts A) Inactivation of GST by ethacrynic acid (EA) derivatives; B) Structure of EA derivatives; and C) EA and EA-Boc$_3$Arg (tert-butyl carbamate protected arginine) inhibit GST-α-1 with similar potency.

Small molecules may promote degradation by directing a target protein into the ubiquitylation pathways. Proteins with N-terminal Arg residues are recognized by a specific set of ubiquitin ligases, causing rapid degradation. Degradation may be induced by attaching an Arg to an inhibitor via a linker so that the protein would now appear to have an N-terminal Arg. Glutathione S-transferase α-1 (GSTα-1) was chosen as the model protein, and ethacrynic acid (EA) as the inhibitor (FIG. 10). EA forms a covalent adduct with the active site Cys of GST as shown in FIG. 10A. Modification of the carboxyl group of EA has little effect on inactivation (FIG. 10C). In an attempt to synthesize EA-Arg (1, FIG. 10), its Boc-protected precursor EA-Boc$_3$Arg (2, FIG. 10) was synthesized. Degradation was observed with EA-Boc$_3$Arg (FIG. 5). No degradation was observed when the protein is treated with EA or EA-linker (3, FIG. 10), or in the absence of inhibitor. Degradation was observed in lysates from reticulocytes, HeLa, Cos and NIH 3T3 cells.

Figure 11:
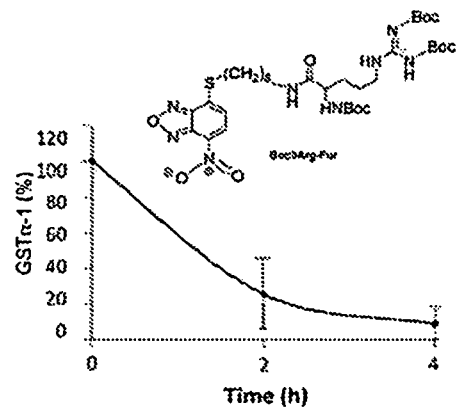
FIG. 11 depicts a graph showing that Fur-Boc$_3$Arg induces the degradation of GSTα-1. Purified C-terminally HA-tagged GST-α-1 was modified with Fur-Boc$_3$Arg and added to NIH 3T3 cell lysates.

A second Boc$_3$Arg-linked GST inhibitor was synthesized to test the generality of the degradation phenomenon. Thiobenzofurazan (Fur) also forms a covalent adduct with GST (FIG. 11). Fur-Boc$_3$Arg-modified GST-α-1 was readily degraded in lysates from NIH 3T3 (FIG. 11). These results demonstrate that Boc$_3$Arg-induced degradation does not depend on the nature of the ligand interacting with GST-α-1.

Additionally, an *E. coli* dihydrofolate reductase (eDHFR) and trimethoprim (TMP) system was used to test the generality of Boc$_3$Arg-induced degradation. TMP is a specific inhibitor of DHFR with poor affinity for the mammalian enzymes. TMP can be readily modified at the 4-position of the B ring with retention of potency and selectivity (FIG. 1, compound 22). TMP-linked fluorescent dyes have been used to selectively label eDHFR fusion proteins in cells and cell lysates. Importantly, the interaction between eDHFR and TMP is noncovalent, though dissociation is very slow (T$_{1/2}$~20 minutes). See FIG. 6.

Figure 6:
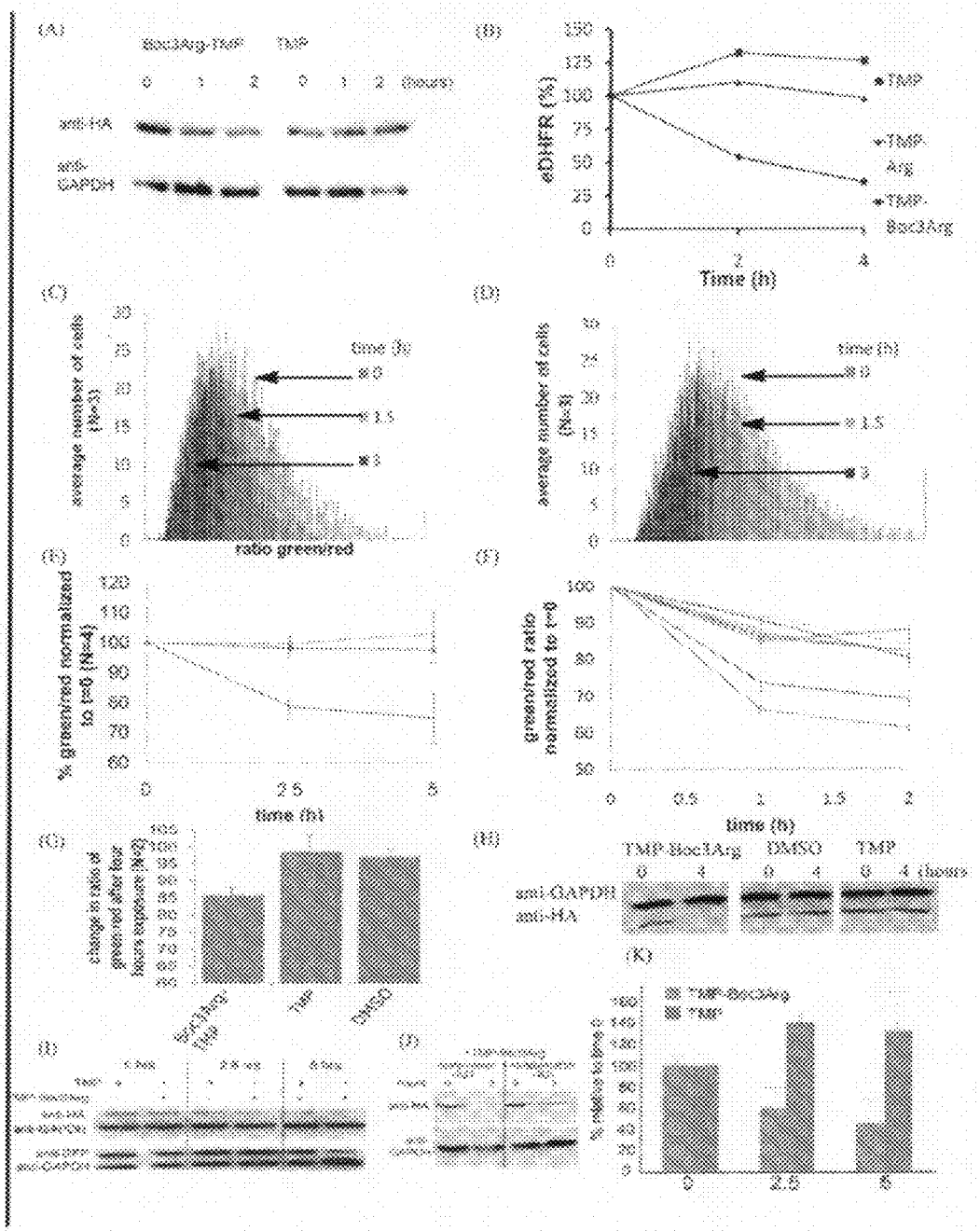
FIG. 6 depicts degradation of eDHFR-HA in cell lysates and degradation of eDHFR fusion proteins in HeLa cells. (A) Degradation of eDHFR in HeLa cells lysates; (B) quantification of panel (A); (C) Global protein stability (GPS) assay. Cells co-express red fluorescent protein (RFP) and DHFR-HA-GFP from a bicistronic construct. Red and green fluorescence was measured by flow cytometry. A time-dependent decrease in ratio of GFP:RFP is observed in the presence of TMP-Boc$_3$Arg; (D) GPS assay in transfected HeLa cells showing no change in GFP:RFP ratio as function of time with TMP; (E) Averaged changes in GFP:RFP ratio as function of time in transfected HeLa cells with no cycloheximide treatment; (F) Averaged changes in GFP:RFP ratio as function of time in transfected HeLa cells with cycloheximide treatment; (G) GPS assay in transfected MCF-7 cells. (H) western blot showing degradation of eDHFR-HA-GFP in transfected HeLa cells; (I) western blot showing that changes in protein concentration are similar to GPS signal changes in HeLa cells transfected with the GPS plasmid; (J) Degradation of eDHFR-HA-GFP in transfected HeLa cells is slower in presence of proteasome inhibitor bortezomib and deubiquitinating inhibitor PU1. No ubiquitination is observed; (K) quantification of panels in (I).
Figure 7:
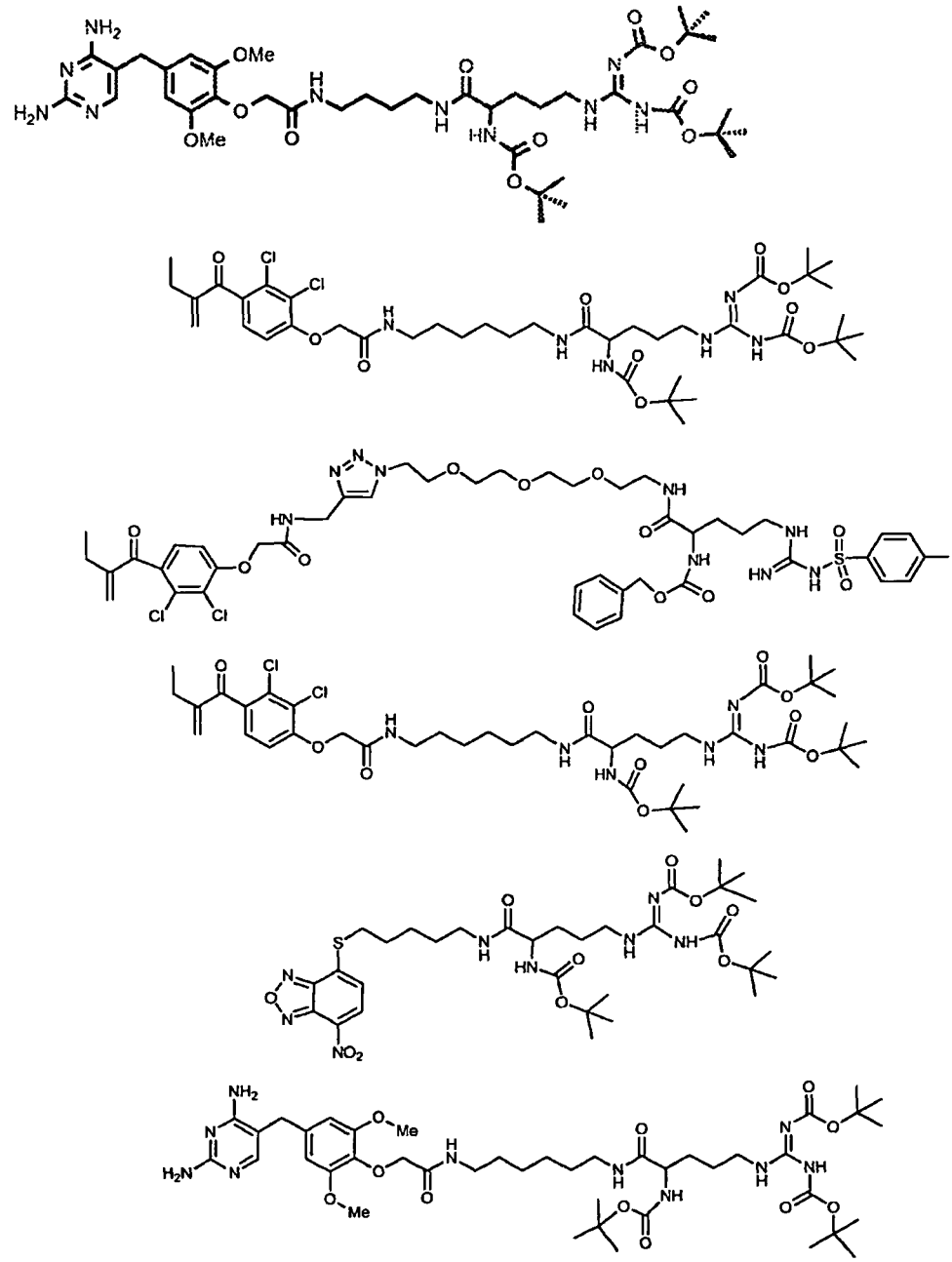
FIG. 7 depicts exemplary compounds of the invention.
Figure 8:
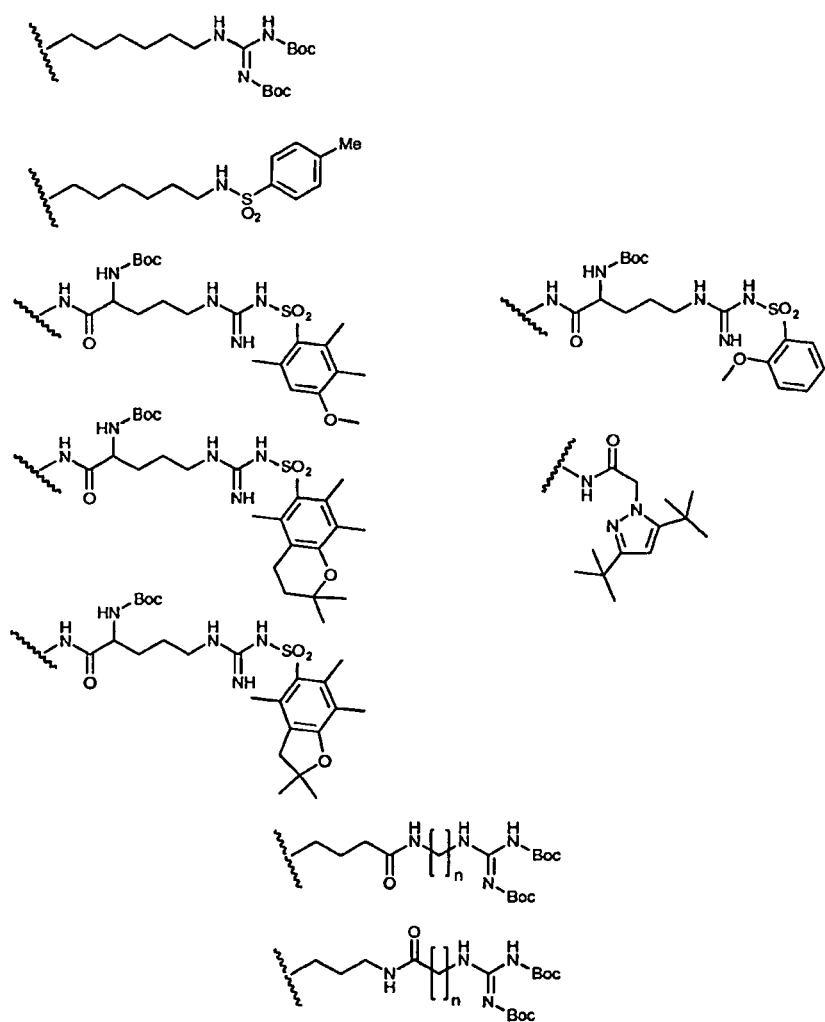
FIG. 8 depicts various exemplary tags of the invention.

As an additional example, eDHFR was fused to green fluorescent protein (GFP) to more readily observe degradation. Like EA-Boc$_3$Arg, TMP-Boc$_3$Arg induced the degradation of its target protein (FIG. 6). Neither TMP nor TMP-Arg induced degradation, nor was degradation observed in the absence of inhibitor. Importantly, a covalent interaction with the target protein is not required.

Protein degradation in whole cells was also assessed. eDHFR-HA-GFP was co-expressed with *Discosoma* sp. red fluorescent protein (RFP) in a bicistronic construct under control of a CMV promoter, with DHFR-HA-GFP translation occurring at the internal ribosome binding site. Thus a single mRNA is responsible for the production of both RFP and DHFR-HA-GFP, so that similar ratios of both proteins should be produced in all transfected cells. Changes in the relative intensities of red and green fluorescence are measured by flow cytometry, providing a facile and quantitative measure of the degradation of DHFR-HA-GFP in living cells and real time. A 40% decrease of eDHFR-HA-GFP was observed in 5 hours in the presence of 80 µM TMP-Boc$_3$Arg as determined by this assay, anti-HA blotting and anti-GFP blotting (FIG. 6). No degradation was observed with TMP alone. Importantly TMP-Boc$_3$Arg did not display cytotoxicity or induce apoptosis at concentrations up to 135 µM as measured by trypan blue staining and PARP cleavage. This experiment demonstrates that TMP-Boc$_3$Arg is cell permeable and can induce selective degradation of an abundant target protein in the context of a whole cell. Importantly, degradation was much faster than commonly observed for RNAi.

Figure 12:
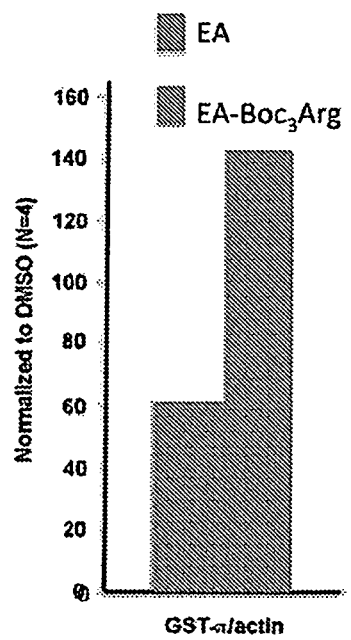
FIG. 12 depicts degradation of endogenous GST-π. Cells were incubated with EA-Boc$_3$Arg for 2 hours. Degradation was monitored by immuno-blotting with anti-GST antibodies. EA=right bar; EA-Boc$_3$-Arg=left bar.

The ability of EA-Boc$_3$Arg to degrade endogenous GST-π in the context of whole cells was also investigated. A 30% depletion in the GST-π signal was observed in the presence of EA-Boc$_3$Arg in two hours (FIG. 12). The Boc$_3$Arg moiety can regulate endogenous protein levels in vivo.

Figure 13:
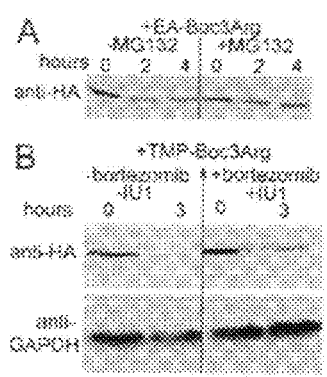
FIG. 13 depicts Boc$_3$Arg induced degradation of the proteasome. A. Degradation of GST-α-1 in cell lysates. B. Degradation of eDHFR-HA-GFP in whole HeLa cells.

Proteasome inhibitors such as MG 132, lactacystin and bortezomib block Boc$_3$Arg-induced degradation (FIG. 13). However, higher molecular weight forms of either GST or eDHFR did not accumulate in the presence of proteasome inhibitors, suggesting that ubiquitylation was not required for degradation. High molecular weight forms still did not appear when deubiquitylating enzyme inhibitors ubiquitin aldehyde or IU1 were included with proteasome inhibitors (IU1 is an inhibitor of USP14). While it can often be difficult to detect ubiquitylation, these observations suggest that the Boc$_3$Arg group induces degradation of the target protein by a novel mechanism of action that is independent of the ubiquitin pathways and therefore distinct from PROTACs.

The effects of TMP-Boc$_3$Arg on the stability of eDHFR. As expected, the association of TMP with eDHFR increases the melting point by ~10° C. (data not shown). A similar increase is observed when eDHFR is treated with another TMP-linked moiety, TMP-DOPA (data not shown), as expected given that modifications of the 4 position of the B ring extend into solvent and therefore have negligible effects on the affinity of TMP. In contrast, a smaller increase in stability is observed in the presence of TMP-Boc$_3$Arg. These observations indicate that the Boc$_3$Arg group interacts with eDHFR.

Protein-Binding Moieties

The protein-binding moieties of the invention are molecular structures which bind target proteins. These protein binding moieties are covalently linked to tags to form the compounds of the invention and provide the linkage between these two elements of the compounds of the invention. When the protein-binding moiety of a compound of the invention binds to a given target protein it presents the tag to trigger the degradation of the protein.

In certain embodiments, the protein-binding moieties are derived from small organic molecules defined by binding to a predetermined target molecule, having a molecular weight from about 50 to about 30,000 and with a binding affinity of greater than about $10^5$ M$^{-1}$ for the target protein of interest. The binding affinity in an advantageous embodiment is greater than about $10^6$ M$^{-1}$. The molecular weight in an advantageous embodiment is between about 50 and about 3,000. The binding affinity in a more advantageous embodiment is greater than about $10^8$ M$^{-1}$. The molecular weight in certain embodiments is between about 100 and about 2,000.

Also target protein binding elements can be selected based on having at least one the following characteristics; less than 50H-bond donors, MW less than 5,000, C log P or M Log P (calculated log P, based on the Pomona College Medicinal Chemistry program C log P or using Molecular Design Limited MACCS and ISIS based programs M log P, log P (the logarithm of the octanol/water partition coefficient) less than 6, sum of N's and O's (a rough measure of H-bond acceptors) less than 100.

Also target protein binding elements can be selected based having on at least one the following characteristics; less than 5H-bond donors, MW less than 500, C log P or M Log P less than 5, sum of N's and O's (a rough measure of H-bond acceptors) less than 10.

Also target protein binding elements can be selected based on having two or more combinations of the following characteristics; less than 5H-bond donors, MW less than 500, C log P or M Log P less than 5, sum of N's and O's (a rough measure of H-bond acceptors) less than 10 (Lipinski C A, 1997, Adv. Drug Delivery Rev. 23, 3-25).

In certain embodiments, protein-binding moieties are different from peptides, proteins and DNA and RNA in that they are not highly charged or polar, are readily absorbed into the body due to the size and hydrophobicity. Also one of the other key properties of target protein binding elements is the stability relative to proteins which are stable within narrow ranges of temperature, pH and ionic strength due to the need to maintain a give structural conformation of the folded polypeptide chain. Peptides although not as sensitive to the physical properties of an environment are relatively unsuitable as drugs due to the poor biological stability, short half-life and poor bioavailability within cells and are not considered compounds of the invention.

Some examples of molecules which have moieties desired in a target protein binding element include drug molecules and molecules selected for binding and/or inhibition of various proteins functions, for example; ethacrynic acid, trimethoprim, fluorescein, biotin, antigens, L-deprenyl, Omeprazole, Clavulanate, organoarsenical compounds such as 4',5'-bis(1,3,2-dithioarsolan-2-yl)fluorescein, p-aminophenylarsine oxide, p-aminophenylarsine oxide, chicoric acid, captopril, enalapril, lovastatin, proscar, indinivar, zileuton, L-372,460 (J. Med Chem 41, 401, 1998), apomorphine, N-n-propylnorapomorphine, dihydrexidine, quinpirole, clozapine, haloperidol, nitrocaramiphen, iodocaramiphen, thiobenzofurazan derivatives, O$^6$-alkylguanine derivatives, and O$^2$-benzylcytosine derivatives.

It is evident from the small sample above that numerous examples exist of chemistries that could form the basis of chemistries for protein binding moieties. Also the numerous nature of these potential protein binding moieties is illustrative of the potential ease with which such moieties can be discovered using routine experimentation.

Compounds of the invention include small molecules used in veterinary, agricultural, food and environmental applications where a biological effect is generated. Examples of compounds of the invention are fungicides, herbicides, pesticides, algaecides, insecticides, anti-virals, anti-parasitics etc. In addition compounds of the invention are also molecules able to form covalent bonds with the target proteins of interest, such as suicide inhibitors. Examples of well know drugs able to from covalent bonds, are as follows; L-deprenyl (Gerlach, M et al 1992, Eur. J. Pharmacol. 226, 97-108), Omeprazole (Howden, C W. 1991, Clin. Pharmacokinet, 20, 38-49) and Clavulanate (Neu, H C. 1990, J. Am. Acad. Dermatol, 22, 896-904). In addition to these well known molecules are a considerable number of other small molecules known to form covalent bonds specifically with various proteins. Also considered compounds of the invention are enzyme substrates that are used to covalently modify proteins (such as farnesylation, phosphorylation, glycosylation, and gerenylation), where the natural enzyme substrate is modified in such a way that it contains a tag.

Targets of the Protein-Binding Moiety

Targets of the target protein-binding moiety are numerous and are selected from proteins and proteins that are expressed in a cell such that at least a portion of the sequences is available within the cell. The term protein includes all sequences of amino acids greater than two and includes peptides. Below is a partial list of target proteins. Any protein in eukaryotic cells are targets for degradation mediated by the compounds of the invention. Those of special interest are those which are involved in diseases or disease processes included; are infectious diseases of viral, microbial, and parasitic nature, metabolic diseases, aging, environmental diseases, genetic diseases, life style diseases.

Also protein targets which are involved in performance enhancement are also targets, such as those involved in growth and development, memory, and sensory perception.

Examples of viruses contemplated as targets of the subject invention are HIV1, HIV2, HLTV, CMV, HPV, HSV, hepatitis, HBV, HCV, HAV, HDV, HGV, influenza A, influenza B, influenza C, rhinoviruses, rotaviruses, entroviruses, Ebola, polio, chicken pox, RSV, coronavirus, adenoviruses, parainfluenza 3, coxsackie A, and epstein-barr virus.

The following are example of targets of the protein-binding moieties of the subject invention, which include:

Receptors: CD124, B7.1 and B7, TNFR1m (p55), TNFR2 (p75), Bcl/Bax, thioredoxin interacting protein and other partners in the apotosis pathways, C5a receptor, CXCR1, CXCR2, 5HT receptors, dopamine receptors, G proteins, ie Gq, histamine receptors, chemokine receptors, JAK/STAT cf ligand, RXR and similar, CD4, CD5, IL-2 receptor, IL-1 receptor, TNF-alphaR, ICAM1, VCAM, VLA-4 integrin, selectins, CD40/CD40L, neurokinin and receptors, Ras/Raf/MEK/ERK pathway, vascular endothelial growth factor, oxytocin receptor, microsomal transfer protein inhibitor, angiotensin II, glycine receptor, noradrenaline reuptake receptor, endothelin receptors, neuropeptide Y and receptor, adenosine receptors, purinergic receptors (P2Y1, P2Y2, P2Y4, P2Y6, P2×1-7), TrkA a receptor for NGF, beta-amyloid, tyrosine kinase Flk-1/KDR, vitronectin receptor, integrin receptor, Her-2/neu, MCH receptor, IL-4 receptor alpha chain and the Toll-like receptors and human homologue, FKHR and AFX or the human homologues of daft, daf 16 and age 1.

Enzymes: NADPH oxidase, HMG-CoA reductase, PDE V phosphodiesterase type, PDE IV phosphodiesterase type 4, PDEI, PDEII, PDEIII, squalene cyclase inhibitor, nitric oxide (NO) synthase, cyclo-oxygenase 1, cyclo-oxygenase 2,5-lipoxygenase, tryptase serine protease, thymidylate synthase, purine nucleoside phosphorylase, GAPDH trypanosomal, glycogen phosphorylase, Carbonic anhydrase, HIV 1 protease, HIV 1 integrase, influenza, neuraminidase, hepatitis B reverse transcriptase, tyrosine kinases, CD23, tyrosine kinase p56 lck, inosine monophosphate dehydrogenase, p38 MAP Kinase, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-1) protease, cytomegalovirus (CMV) protease, poly (ADP-ribose) polymerase, cyclin dependent kinases, 5 alpha reductase inhibitors, adenosine kinase and AMP deaminase, farnesyltransferases, geranylgeranyl transferase, telomerase, cytosolic phospholipase A2, EGF receptor tyrosine kinase.

Membrane Transporters: Sodium channel, Ca++ channels, multi drug resistance (MDR), protein P-glycoprotein (and MRP), bile acid transporter.

Insecticide target examples include, ecdysone 20-monooxygenase, ion channel of the GABA gated chloride channel, acetylcholinesterase, voltage-sensitive sodium channel protein, calcium release channel, and chloride channels.

Herbicide target examples include Acetyl-CoA carboxylase, adenylosuccinate synthetase, protoporphyrinogen oxidase, and enolpyruvylshikimate-phosphate synthase.

Targets for anti-parasitic drug development include: *Leishmania*, proteins of the sterol synthesis pathway, *Plasmodium*, dihydrofolate reductase, dihydrofolate reductase-thymidylate synthase (bifunctional) resistance known due to mutations in the gene for this enzyme, heme polymerase, dihydroorate dehydrogenase, *Trypanosoma*, ornithine decarboxylase, trypanothione reductase. Ornithine decarboxylase of the *trypanosoma* also represents an ideal candidate for destruction due to its long half-life and low turn over in *trypanosoma*. It has also been suggested that the shikimate pathway, which is a target for herbicide development, would also be of value in the development of anti-parasitics for parasites of the phylum Apicomplexa (ie. *Plasmodium falciparum, Cryptosporidium parvum* and *Toxoplasma gondii*) as it absent from mammals.

Targets in a fusion protein include, but are not limited to: GST, DHRF, SNAP, CLIP, and HALO.

Targets of the subject invention also include proteins that are involved in the performance of a cell and/or organism. Performance characters of a cell and/or organism are those characters which are considered desirable traits which a cell and/or organism has in some part. These performance characters may be present in other cells or organisms and be desired in cells and/or organisms which do not posses them. Examples of what are considered performance characters are, flower color, fragrances, specific shapes and colors in organisms such a cats and dogs, disease resistance, growth rates, size, taste, alcohol yield from yeast. Thus performance characters are generally things that are desired in cells and organisms used either in the production of desired products or in the production of esthetical value (look, taste, feel, smell and sound).

In the case of flower color (considered an esthetical value), the proteins involved in the biosynthesis of flavonoids, carotenoids and anthocyanins; including flavanone 3-hydroxylase, anthocyanin synthase, dihydroflavonol 4-reductase, flavonoid 3',5'-hydroxylase, anthocyanin 5-aromatic acyltransferase, UDP-glucose: flavonoid 3-O-glucosyltransferase, anthocyanin rhamnosyltransferase, anthocyanin 3'-methyltransferase, anthocyanin 3'5'-methyltransferase, leucoanthocyanidin dioxygenase, anthocyanidin synthase, anthocyanin acyltransferase, chalcone synthase, chalcone flavanone isomerase, glutathione S-transferase, one considered as targets of the subject invention involved in performance characteristics. In addition to the proteins involved in the synthesis of flower color, the proteins involved in the regulation of the expression of the synthases and other proteins involved in the production of flower color are also considered targets of the subject invention. Examples of the regulatory genes include the R and C1 gene families, an2 and jaf13, the delila gene. Quattrocchio F. 1998, Plant J. 13(4), 475-488.

Other potential target molecules of the subject invention include targets as described above but also targets in all eukaryotic organisms. Potential targets exist in agriculture, veterinary and environmental fields. For example in the agricultural field, molecules which are selective in action and non-toxic are highly desirable for use as herbicides, anti-virals, anti-parasitics, growth modulators and drugs; thus target molecules can be selected from certain animals, plants, viruses and parasites of interest to agriculture. In the veterinary field anti-virals, anti-parasitics, antibiotics, growth modulators, anti-inflammatory and drugs are of interest and target molecules can be selected from certain animals, viruses and parasites of interest in veterinary science. In the environmental field the potential targets are the same as for agricultural but the aims are to control selectively certain populations either positively as in the case of an endangered species but also negatively where a population has expanded its environment or where a foreign organism is undesirable to a given ecosystem. Thus it is understood by those skilled in the art that the ability to modulate the level of a selected target molecule could have wide ranging effects in very diverse areas of science, technology and human endeavors.

Compounds

One aspect of the invention relates to a compound which comprises: a protein-binding moiety which binds a protein, a tag which promotes the degradation of said protein, and a covalent linker which connects the protein-binding moiety to the tag.

In certain embodiments, the invention relates to any one of the aforementioned compounds, wherein the excessive expression of the protein in a mammal is the cause, at least in part, of a disease or disorder.

In certain embodiments, the invention relates to any one of the aforementioned compounds, wherein the protein is selected from the group consisting of glutathione-S-transferase α1 (GST), dihydrofolate reductase (DHFR), botulinum toxin (BoNT), the mutant form of IMP dehydrogenase type 1 (IMPDH1), Bcr-Abl, and thioredoxin interacting protein. The mutant form of IMP dehydrogenase type 1 (IMPDH1) causes retinitis pigmentosa.

In certain embodiments, the invention relates to any one of the aforementioned compounds, wherein the protein is a fusion protein comprising a first protein and a second protein. In certain embodiments, the first protein is GST, DHFR, SNAP, CLIP, or HALO. In certain embodiments, the tag promotes degradation of the second protein. In certain embodiments, the first protein is GST. In certain embodiments, the first protein is GST; and the protein-binding moiety is ethacrynic acid. In certain embodiments, the first protein is GST; and the protein-binding moiety is a thiobenzofurazan derivative. In certain embodiments, the first protein is DHFR; and the protein-binding moiety is a trimethoprim derivative. In certain embodiments, the first protein is SNAP; and the protein-binding moiety is an $O^6$-alkylguanine derivative or a benzylguanine derivative. In certain embodiments, the first protein is CLIP; and the protein-binding moiety is an $O^2$-benzylcytosine derivative. In certain embodiments, the first protein is HALO; and the protein-binding moiety is an alkyl halide derivative. See FIG. 2. Importantly, the terms "first protein" and "second protein" do not refer to the order of the proteins in the fusion construct.

In certain embodiments, the invention relates to any one of the aforementioned compounds, wherein the protein-binding moiety which binds the protein is an inhibitor of the activity of the protein.

In certain embodiments, the invention relates to any one of the aforementioned compounds, wherein the covalent linker is bonded to an oxygen, sulfur or nitrogen of the protein-binding moiety.

In certain embodiments, the invention relates to any one of the aforementioned compounds, wherein the covalent linker comprises an alkylene.

In certain embodiments, the invention relates to any one of the aforementioned compounds, wherein the covalent linker is aminoalkyleneamino.

In certain embodiments, the invention relates to any one of the aforementioned compounds, wherein the covalent linker is —N(H)[CH$_2$]$_n$N(H)—; and n is 1-10 inclusive.

In certain embodiments, the invention relates to any one of the aforementioned compounds, wherein the covalent linker is —(OCH$_2$CH$_2$)$_n$O—; and n is 1-10 inclusive.

In certain embodiments, the invention relates to any one of the aforementioned compounds, wherein the covalent linker is —(OCH$_2$CH$_2$)$_n$NH—; and n is 1-10 inclusive.

In certain embodiments, the invention relates to any one of the aforementioned compounds, wherein the covalent linker comprises a triazolyl moiety.

In certain embodiments, the invention relates to any one of the aforementioned compounds, wherein n is 4-8 inclusive.

In certain embodiments, the invention relates to any one of the aforementioned compounds, wherein n is 6.

In certain embodiments, the invention relates to any one of the aforementioned compounds, wherein the tag comprises an oxidized amino acid, lipid oxidative degradation product, N-end rule residue or a substituted arginine.

In certain embodiments, the invention relates to any one of the aforementioned compounds, wherein the tag comprises a guanidinium.

In certain embodiments, the invention relates to any one of the aforementioned compounds, wherein the tag is

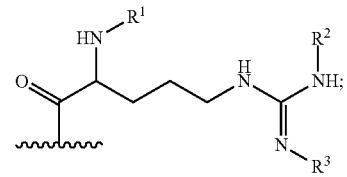

$R^1$ is alkoxycarbonyl, $R^2$ is alkoxycarbonyl and $R^3$ is alkoxycarbonyl.

In certain embodiments, the invention relates to any one of the aforementioned compounds, wherein $R^1$, $R^2$ and $R^3$ are t-butyloxycarbonyl.

In certain embodiments, the invention relates to any one of the aforementioned compounds, wherein the tag is

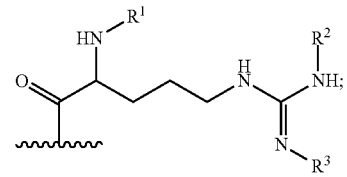

$R^1$ is aralkyloxycarbonyl or heteroaralkyloxycarbonyl, $R^2$ is arylsulfonyl or heteroarylsulfonyl; and $R^3$ is hydrogen.

In certain embodiments, the invention relates to any one of the aforementioned compounds, wherein $R^1$ is t-butyloxycarbonyl; $R^2$ is 4-methylphenylsulfonyl; and $R^3$ is hydrogen.

In certain embodiments, the invention relates to any one of the aforementioned compounds, wherein the tag is

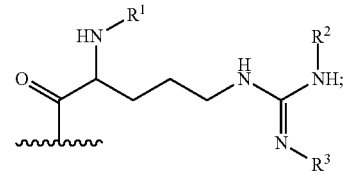

$R^1$ is aralkyloxycarbonyl or heteroaralkyloxycarbonyl, $R^2$ is aralkyloxycarbonyl or heteroaralkyloxycarbonyl; and $R^3$ is aralkyloxycarbonyl or heteroaralkyloxycarbonyl.

In certain embodiments, the invention relates to any one of the aforementioned compounds, wherein the tag is

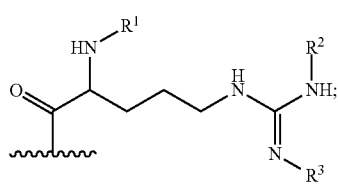

$R^1$ is benzyloxycarbonyl, $R^2$ is benzyloxycarbonyl; and $R^3$ is benzyloxycarbonyl.

In certain embodiments, the invention relates to any one of the aforementioned compounds, wherein the tag is selected from the group consisting of:

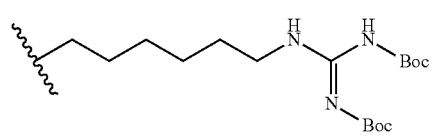

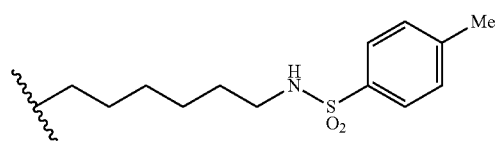

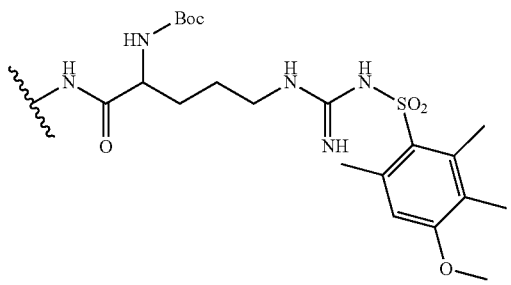

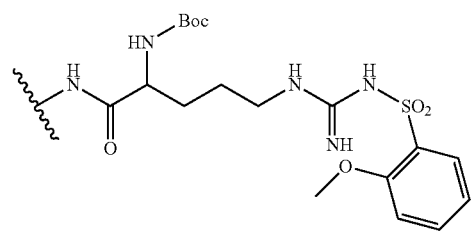

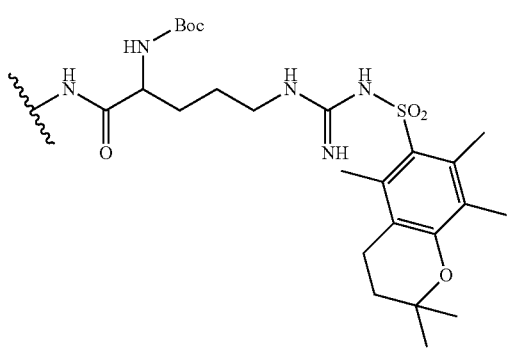

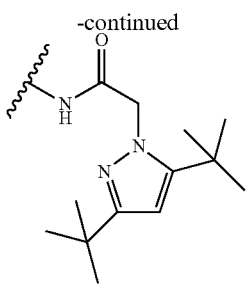

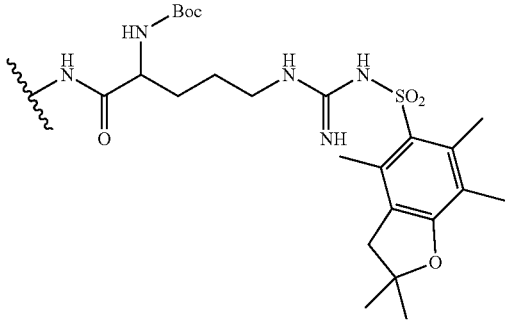 [SMILES: *NC(=O)C(CCCNC(=N)NS(=O)(=O)c1c(C)c(C)c2c(c1C)CC(C)(C)O2)NC(=O)OC(C)(C)C]

Another aspect of the invention relates to a compound represented by formula I, or a pharmaceutically acceptable salt thereof,

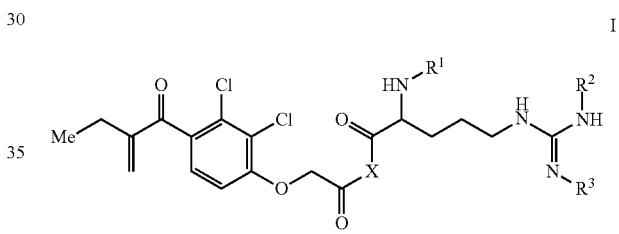

I wherein
X is aminoalkyleneamino;
$R^1$ is alkoxycarbonyl;
$R^2$ is alkoxycarbonyl; and
$R^3$ is alkyloxycarbonyl.

In certain embodiments, the invention relates to any one of the aforementioned compounds, wherein X is —N(H)[CH$_2$]$_n$N(H)—; and n is 1-10 inclusive.

In certain embodiments, the invention relates to any one of the aforementioned compounds, wherein n is 4-8 inclusive.

In certain embodiments, the invention relates to any one of the aforementioned compounds, wherein n is 6.

In certain embodiments, the invention relates to any one of the aforementioned compounds, wherein $R^1$ is t-butoxycarbonyl.

In certain embodiments, the invention relates to any one of the aforementioned compounds, wherein $R^2$ is t-butoxycarbonyl.

In certain embodiments, the invention relates to any one of the aforementioned compounds, wherein $R^3$ is t-butoxycarbonyl.

In certain embodiments, the invention relates to any one of the aforementioned compounds, wherein $R^1$ is t-butoxycarbonyl; $R^2$ is t-butoxycarbonyl; and $R^3$ is t-butoxycarbonyl.

In certain embodiments, the invention relates to any one of the aforementioned compounds, wherein $R^1$ is t-butoxycarbonyl; $R^2$ is t-butoxycarbonyl; $R^3$ is t-butoxycarbonyl; X is —N(H)[CH$_2$]$_n$N(H)—; and n is 1-10 inclusive.

In certain embodiments, the invention relates to any one of the aforementioned compounds, wherein $R^1$ is t-butoxycarbonyl; $R^2$ is t-butoxycarbonyl; $R^3$ is t-butoxycarbonyl; X is —N(H)[CH$_2$]$_n$N(H)—; and n is 4-8 inclusive.

In certain embodiments, the invention relates to any one of the aforementioned compounds, wherein $R^1$ is t-butoxycarbonyl; $R^2$ is t-butoxycarbonyl; $R^3$ is t-butoxycarbonyl; X is —N(H)[CH$_2$]$_n$N(H)—; and n is 6.

Another aspect of the invention relates to a compound represented by formula II, or a pharmaceutically acceptable salt thereof,

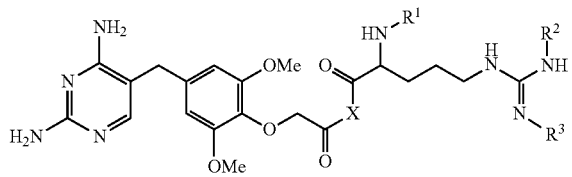

wherein
X is aminoalkyleneamino;
$R^1$ is aralkyloxycarbonyl or heteroaralkyloxycarbonyl;
$R^2$ is arylsulfonyl or heteroarylsulfonyl; and
$R^3$ is hydrogen.

In certain embodiments, the invention relates to any one of the aforementioned compounds, wherein X is —N(H)[CH$_2$]$_n$N(H)—; and n is 1-10 inclusive.

In certain embodiments, the invention relates to any one of the aforementioned compounds, wherein n is 4-8 inclusive.

In certain embodiments, the invention relates to any one of the aforementioned compounds, wherein n is 6.

In certain embodiments, the invention relates to any one of the aforementioned compounds, wherein $R^1$ is aralkyloxycarbonyl.

In certain embodiments, the invention relates to any one of the aforementioned compounds, wherein $R^1$ is benzyloxycarbonyl.

In certain embodiments, the invention relates to any one of the aforementioned compounds, wherein $R^2$ is arylsulfonyl.

In certain embodiments, the invention relates to any one of the aforementioned compounds, wherein $R^2$ is 4-methylphenylsulfonyl.

In certain embodiments, the invention relates to any one of the aforementioned compounds, wherein $R^1$ is t-butoxycarbonyl; and $R^2$ is arylsulfonyl.

In certain embodiments, the invention relates to any one of the aforementioned compounds, wherein $R^1$ is t-butoxycarbonyl; and $R^2$ is 4-methylphenylsulfonyl.

In certain embodiments, the invention relates to any one of the aforementioned compounds, wherein $R^1$ is t-butoxycarbonyl; $R^2$ is 4-methylphenylsulfonyl; X is —N(H)[CH$_2$]$_n$N(H)—; and n is 1-10 inclusive.

In certain embodiments, the invention relates to any one of the aforementioned compounds, wherein $R^1$ is t-butoxycarbonyl; $R^2$ is 4-methylphenylsulfonyl; X is —N(H)[CH$_2$]$_n$N(H)—; and n is 4-8 inclusive.

In certain embodiments, the invention relates to any one of the aforementioned compounds, wherein $R^1$ is t-butoxycarbonyl; $R^2$ is 4-methylphenylsulfonyl; X is —N(H)[CH$_2$]$_n$N(H)—; and n is 6.

Another aspect of the invention relates to a compound represented by formula III, or a pharmaceutically acceptable salt thereof,

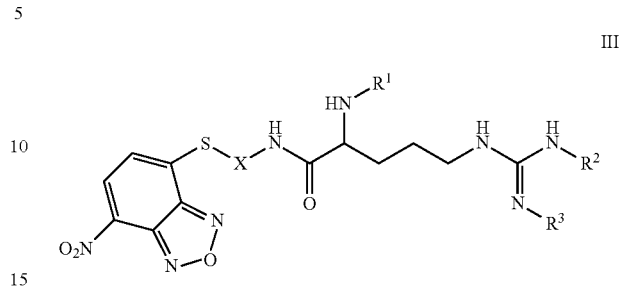

wherein
X is alkylene;
$R^1$ is aralkyloxycarbonyl or heteroaralkyloxycarbonyl;
$R^2$ is aralkyloxycarbonyl or heteroaralkyloxycarbonyl; and
$R^3$ is aralkyloxycarbonyl or heteroaralkyloxycarbonyl.

In certain embodiments, the invention relates to any one of the aforementioned compounds, wherein X is —(CH$_2$)$_n$—; and n is 1-10 inclusive.

In certain embodiments, the invention relates to any one of the aforementioned compounds, wherein n is 4-8 inclusive.

In certain embodiments, the invention relates to any one of the aforementioned compounds, wherein n is 6.

In certain embodiments, the invention relates to any one of the aforementioned compounds, wherein $R^1$ is aralkyloxycarbonyl.

In certain embodiments, the invention relates to any one of the aforementioned compounds, wherein $R^1$ is benzyloxycarbonyl.

In certain embodiments, the invention relates to any one of the aforementioned compounds, wherein $R^2$ is aralkyloxycarbonyl.

In certain embodiments, the invention relates to any one of the aforementioned compounds, wherein $R^2$ is benzyloxycarbonyl.

In certain embodiments, the invention relates to any one of the aforementioned compounds, wherein $R^3$ is aralkyloxycarbonyl.

In certain embodiments, the invention relates to any one of the aforementioned compounds, wherein $R^3$ is benzyloxycarbonyl.

In certain embodiments, the invention relates to any one of the aforementioned compounds, wherein $R^1$ is aralkyloxycarbonyl; $R^2$ is aralkyloxycarbonyl; $R^3$ is aralkyloxycarbonyl; X is —(CH$_2$)$_n$—; and n is 1-10 inclusive.

In certain embodiments, the invention relates to any one of the aforementioned compounds, wherein $R^1$ is benzyloxycarbonyl; $R^2$ is benzyloxycarbonyl; $R^3$ is benzyloxycarbonyl; X is —(CH$_2$)$_n$—; and n is 6.

Another aspect of the invention relates to a compound represented by formula IV, or a pharmaceutically acceptable salt thereof,

IV

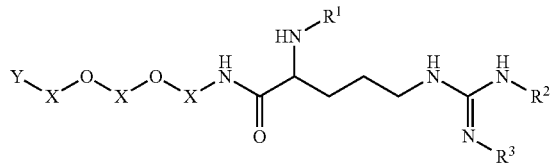

wherein
X is alkylene;
Y is chloro, bromo, or iodo;
$R^1$ is aralkyloxycarbonyl or heteroaralkyloxycarbonyl;
$R^2$ is aralkyloxycarbonyl or heteroaralkyloxycarbonyl; and
$R^3$ is aralkyloxycarbonyl or heteroaralkyloxycarbonyl.

In certain embodiments, the invention relates to any one of the aforementioned compounds, wherein X is —(CH$_2$)$_n$—; and n is 1-10 inclusive.

In certain embodiments, the invention relates to any one of the aforementioned compounds, wherein $R^1$ is aralkyloxycarbonyl.

In certain embodiments, the invention relates to any one of the aforementioned compounds, wherein $R^1$ is benzyloxycarbonyl.

In certain embodiments, the invention relates to any one of the aforementioned compounds, wherein $R^2$ is aralkyloxycarbonyl.

In certain embodiments, the invention relates to any one of the aforementioned compounds, wherein $R^2$ is benzyloxycarbonyl.

In certain embodiments, the invention relates to any one of the aforementioned compounds, wherein $R^3$ is aralkyloxycarbonyl.

In certain embodiments, the invention relates to any one of the aforementioned compounds, wherein $R^3$ is benzyloxycarbonyl.

In certain embodiments, the invention relates to any one of the aforementioned compounds, wherein $R^1$ is aralkyloxycarbonyl; $R^2$ is aralkyloxycarbonyl; $R^3$ is aralkyloxycarbonyl; X is —(CH$_2$)$_n$—; and n is 1-10 inclusive.

In certain embodiments, the invention relates to any one of the aforementioned compounds, wherein Y is chloro.

Another aspect of the invention relates to a compound represented by formula V, or a pharmaceutically acceptable salt thereof,

V

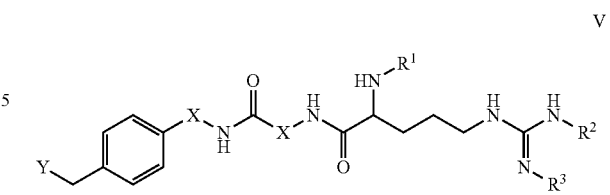

wherein
X is alkylene;
Y is chloro, bromo, or iodo;
$R^1$ is aralkyloxycarbonyl or heteroaralkyloxycarbonyl;
$R^2$ is aralkyloxycarbonyl or heteroaralkyloxycarbonyl; and
$R^3$ is aralkyloxycarbonyl or heteroaralkyloxycarbonyl.

In certain embodiments, the invention relates to any one of the aforementioned compounds, wherein X is —(CH$_2$)$_n$—; and n is 1-10 inclusive.

In certain embodiments, the invention relates to any one of the aforementioned compounds, wherein $R^1$ is aralkyloxycarbonyl.

In certain embodiments, the invention relates to any one of the aforementioned compounds, wherein $R^1$ is benzyloxycarbonyl.

In certain embodiments, the invention relates to any one of the aforementioned compounds, wherein $R^2$ is aralkyloxycarbonyl.

In certain embodiments, the invention relates to any one of the aforementioned compounds, wherein $R^2$ is benzyloxycarbonyl.

In certain embodiments, the invention relates to any one of the aforementioned compounds, wherein $R^3$ is aralkyloxycarbonyl.

In certain embodiments, the invention relates to any one of the aforementioned compounds, wherein $R^3$ is benzyloxycarbonyl.

In certain embodiments, the invention relates to any one of the aforementioned compounds, wherein $R^1$ is aralkyloxycarbonyl; $R^2$ is aralkyloxycarbonyl; $R^3$ is aralkyloxycarbonyl; X is —(CH$_2$)$_n$—; and n is 1-10 inclusive.

In certain embodiments, the invention relates to any one of the aforementioned compounds, wherein Y is chloro.

Another aspect of the invention relates to a compound represented by formula VI, or a pharmaceutically acceptable salt thereof,

VI

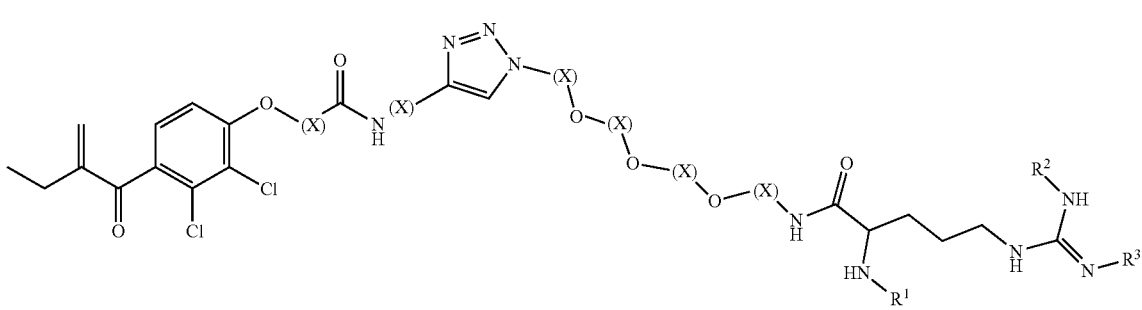

wherein

X is alkylene;

R¹ is aralkyloxycarbonyl or heteroaralkyloxycarbonyl;

R² is aralkyloxycarbonyl or heteroaralkyloxycarbonyl; and

R³ is aralkyloxycarbonyl or heteroaralkyloxycarbonyl.

In certain embodiments, the invention relates to any one of the aforementioned compounds, wherein X is —$(CH_2)_n$—; and n is 1-10 inclusive.

In certain embodiments, the invention relates to any one of the aforementioned compounds, wherein R¹ is aralkyloxycarbonyl.

In certain embodiments, the invention relates to any one of the aforementioned compounds, wherein R¹ is benzyloxycarbonyl.

In certain embodiments, the invention relates to any one of the aforementioned compounds, wherein R² is aralkyloxycarbonyl.

In certain embodiments, the invention relates to any one of the aforementioned compounds, wherein R² is benzyloxycarbonyl.

In certain embodiments, the invention relates to any one of the aforementioned compounds, wherein R³ is aralkyloxycarbonyl.

In certain embodiments, the invention relates to any one of the aforementioned compounds, wherein R³ is benzyloxycarbonyl.

In certain embodiments, the invention relates to any one of the aforementioned compounds, wherein R¹ is aralkyloxycarbonyl; R² is aralkyloxycarbonyl; R³ is aralkyloxycarbonyl; X is —$(CH_2)_n$—; and n is 1-10 inclusive.

Many of the compounds of the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Certain compounds of the invention and their salts may exist in more than one crystal form and the present invention includes each crystal form and mixtures thereof.

Certain compounds of the invention and their salts may also exist in the form of solvates, for example hydrates, and the present invention includes each solvate and mixtures thereof.

Certain compounds of the invention may contain one or more chiral centers, and exist in different optically active forms. When compounds of the invention contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the invention contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of the invention and mixtures thereof.

Certain compounds of the invention may exist in different tautomeric forms or as different geometric isomers, and the present invention includes each tautomer and/or geometric isomer of compounds of the invention and mixtures thereof.

Certain compounds of the invention may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of the invention and mixtures thereof.

Certain compounds of the invention may exist in zwitterionic form and the present invention includes each zwitterionic form of compounds of the invention and mixtures thereof.

The present invention also includes pro-drugs. As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., —$C(O)_2H$ or a moiety that contains a carboxylic acid) wherein the free hydrogen is replaced by ($C_1$-$C_4$)alkyl, ($C_2$-$C_{12}$)alkanoyloxymethyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)-alkylcarbamoyl-($C_1$-$C_2$)alkyl and piperidino-, pyrrolidino- or morpholino($C_2$-$C_3$)alkyl.

Other exemplary pro-drugs release an alcohol or amine of a compound of the invention wherein the free hydrogen of a hydroxyl or amine substituent is replaced by ($C_1$-$C_6$) alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyl-oxymethyl, N—($C_1$-$C_6$)alkoxycarbonyl aminomethyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, —$P(O)(OH)_2$, —$P(O)(O(C_1$-$C_6)$alkyl$)_2$ or glycosyl (the radical resulting from detachment of the hydroxyl of the hemiacetal of a carbohydrate).

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991). Protected forms of the inventive compounds are included within the scope of this invention.

The term "chemically protected form," as used herein, pertains to a compound in which one or more reactive functional groups are protected from undesirable chemical reactions, that is, are in the form of a protected or protecting group (also known as a masked or masking group). It may be convenient or desirable to prepare, purify, and/or handle the active compound in a chemically protected form.

By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)$CH_3$, —OAc).

For example, an aldehyde or ketone group may be protected as an acetal or ketal, respectively, in which the carbonyl group (C(=O)) is converted to a diether (C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRC(=O)R) or a urethane (—NRC(=O)OR), for example, as: a methyl amide (—NHC(=O)$CH_3$); a benzyloxy amide (—NHC(=O) $OCH_2C_6H_5$NHCbz); as a t-butoxy amide (—NHC(=O) OC($CH_3$)$_3$, —NHBoc); a 2-biphenyl-2-propoxy amide (—NHC(=O)OC($CH_3$)$_2C_6H_4C_6H_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide.

For example, a thiol group may be protected as a thioether (—SR), for example, as: a benzyl thioether; or an acetamidomethyl ether (—$SCH_2$NHC(=O)$CH_3$).

Methods

In certain embodiments, the present invention provides an approach to protein therapeutics using targeted protein and/or targeted polypeptide degradation. The current paradigm in screening small molecule libraries is to find inhibitors of enzymatic processes that are causal in disease. However, the number of small molecules that both specifically bind to, and inhibit the function of a polypeptide (i.e., via inhibiting one or more active sites) is extremely small. It has recently been recognized that inhibitors with long residence times on their targets are more efficacious in vivo. This observation has led to the idea that a perfect inhibitor irreversibly inactivates its target, so that only new synthesis of the target protein restores activity. Obviously, an inhibitor that induces degradation is perfect by this definition. Furthermore, as active sites tend to be highly conserved or convergent, compounds that inhibit the active site of a targeted protein and/or polypeptide may also exhibit undesirable cross-reactivity with active sites of one or more non-targeted proteins and/or polypeptides. Compounds that target proteins and/or polypeptides for degradation could help limit the degree of this kind of cross-reactivity.

Targeted protein and/or polypeptide degradation is also useful for developing catalytic therapeutic agents. For example, a therapeutic agent of the present invention targets a specific polypeptide to the proteasome for degradation. After degradation, the agent is released and available to target another polypeptide to the proteasome for degradation. This could allow for lower doses of the agent to be used therapeutically, resulting in lower costs and less side effects.

As used herein, a disorder associated with the expression and/or activity of a polypeptide (i.e., "protein-expression related disease") is meant a disease or disorder whose pathology is related at least in part to inappropriate protein expression (e.g., expression at the wrong time and/or in the wrong cell), excessive protein expression or expression of a mutant protein; it includes a disorder, disease or condition which is caused or characterized by a misregulation (e.g., upregulation) of a polypeptide. Protein-expression related diseases can detrimentally affect cellular functions including, but not limited to, cellular proliferation, growth, differentiation, or migration, inter- or intra-cellular communication, tissue function, systemic responses in an organism, susceptibility to pathogenic infections, immune responses, and protection of cells from toxic compounds (e.g., carcinogens, toxins, or mutagens).

In at least certain examples, the compounds disclosed herein can be used in the treatment of protein-expression related diseases such as cellular proliferative disorders, (e.g., cancer). Treatment of cellular proliferative disorders is intended to include inhibition of proliferation including rapid proliferation. As used herein, the term "cellular proliferative disorder" includes disorders characterized by undesirable or inappropriate proliferation of one or more subset(s) of cells in a multicellular organism. The term "cancer" refers to various types of malignant neoplasms, most of which can invade surrounding tissues, and may metastasize to different sites (see, for example, PDR Medical Dictionary 1st edition (1995)). The terms "neoplasm" and "tumor" refer to an abnormal tissue that grows by cellular proliferation more rapidly than normal and continues to grow after the stimuli that initiated proliferation is removed (see, for example, PDR Medical Dictionary 1st edition (1995)). Such abnormal tissue shows partial or complete lack of structural organization and functional coordination with the normal tissue which may be either benign (i.e., benign tumor) or malignant (i.e., malignant tumor).

The language "treatment of cellular proliferative disorders" is intended to include the prevention of the growth of neoplasms in a subject or a reduction in the growth of pre-existing neoplasms in a subject. The inhibition also can be the inhibition of the metastasis of a neoplasm from one site to another. Examples of the types of neoplasms intended to be encompassed by the present invention include but are not limited to those neoplasms associated with cancers of the breast, skin, bone, prostate, ovaries, uterus, cervix, liver, lung, brain, larynx, gallbladder, pancreas, rectum, parathyroid, thyroid, adrenal gland, immune system, neural tissue, head and neck, colon, stomach, bronchi, and/or kidneys.

Cellular proliferative disorders can further include disorders associated with hyperproliferation of vascular smooth muscle cells such as proliferative cardiovascular disorders, e.g., atherosclerosis and restinosis. Cellular proliferation disorders can also include disorders such as proliferative skin disorders, e.g., X-linked ichthyosis, psoriasis, atopic dermatitis, allergic contact dermatitis, epidermolytic hyperkeratosis, and seborrheic dermatitis. Cellular proliferative disorders can further include disorders such as autosomal dominant polycystic kidney disease (ADPKD), mastocystosis, and cellular proliferation disorders caused by infectious agents such as viruses.

Figure 3:
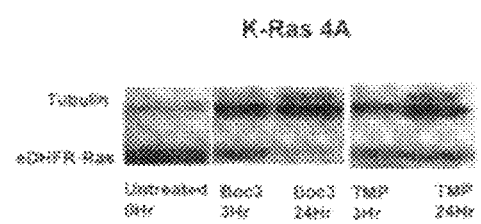
FIG. 3 depicts the degradation of eDHFR-KRas D12 fusion protein. MSCV retrovirus was used to insert eDHFR-KRas D12 fusion gene into NIH3T3 cells. These cells were plated in a 48-well plate and treated with 16 μM of either trimethoprim or trimethoprim-Boc$_3$Arg, and then harvested at the times indicated. eDHFR-Ras contained a FLAG tag at the amino terminus and was measured through western blot with anti-FLAG antibody. Tubulin was used as a loading control.
Figure 4:
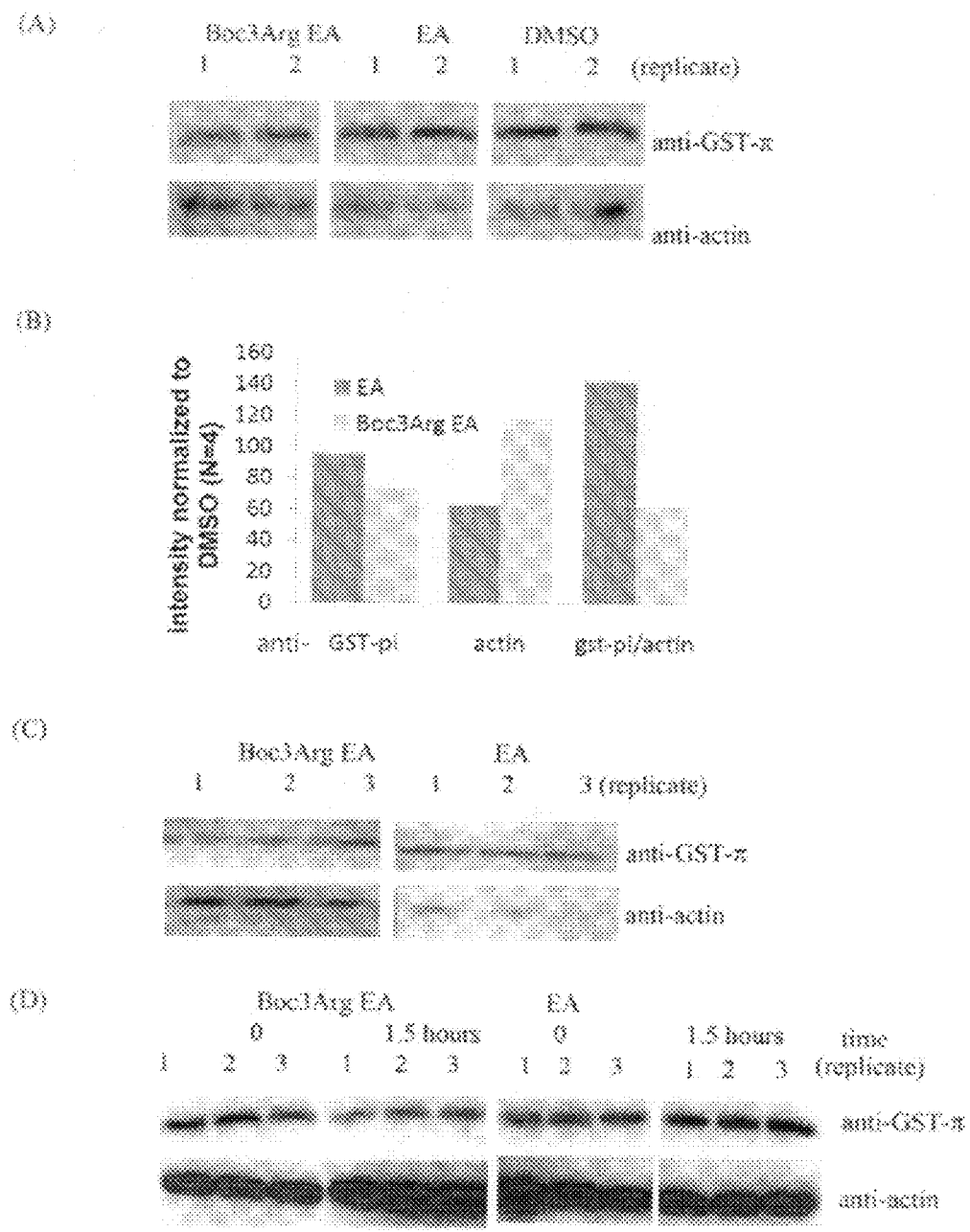
FIG. 4 depicts the degradation of endogenous GST-π by EA-Boc3Arg in Cos-1 and HeLa cells. (A) degradation of endogenous GST-π in Cos-1 cells; (B) quantitation of data in (A); (C) Degradation of endogenous GST-π in cycloheximide treated Cos-1 cells; (D) Degradation of endogenous GST-π in Cycloheximide treated HeLa cell.

In certain embodiments, the invention relates to methods of cancer chemotherapy. For example, mutations in Ras are found in 20-30% of all tumors. Ras is a scaffolding protein, and therefore not amenable to the development of small molecule inhibitors as would be an enzyme or receptor. In certain embodiments, the invention relates to a method of degrading oncogenic Ras. As proof of concept, a Ras-DHFR fusion protein is degraded by trimethoprim-tag. See FIG. 3.

Similarly, transcription factors such as Myc are believed to be targets for anticancer therapy, but it has been difficult to develop small molecules that block transcription factor action. In certain embodiments, the invention relates to a method of degrading Myc.

In certain embodiments, the invention relates to a method of improving currently existing anticancer therapy. Bcr-Abl is the aberrant protein kinase formed in the gene fusion event that is responsible for chronic myelogenous leukemia (CML). Selective Bcr-Abl inhibitors such as imatinib mesylate (i.e., Gleevec®) have been very successful in treating CML. Nonetheless, new therapies are needed to combat resistance. Importantly, simply blocking the kinase activity of the Bcr-Abl kinase is not sufficient to block activation of all its downstream signaling pathways; obviously such kinase activity-independent signaling would be eliminated if Bcr-Abl was degraded. Further, neither imatinib nor the second generation inhibitor dasatinib (DS) induce apoptosis of CML stem cells. This failure to eliminate CML stem cells is believed to cause relapse when drug is withdrawn. In certain embodiments, the invention relates to a method of degrading Bcr-Abl.

In certain embodiments, the invention relates to a method of improving currently existing diabetes therapy. The knockdown of thioredoxin interacting protein (TXNIP) protects against glucose-induced apoptosis. In certain embodiments, the invention relates to a method of degrading TXNIP.

In at least certain examples, the compounds disclosed herein can be used in the treatment of disorders associated with pathogen infection. Disorders associated with infection by pathogens include, but are not limited to, infection by viruses (DNA viruses, RNA viruses, animal viruses, and the like), bacteria (e.g., gram positive bacteria, gram negative bacteria, acid-fast bacteria, and the like), fungi, parasitic microbes, nematodes, and the like.

Compounds disclosed herein are also useful for treating disorders associated with aberrant peptide folding and/or aberrant peptide degradation. Such disorders include, but are not limited to, cellular proliferation disorders, prion diseases (e.g., scrapie, Creutzfeldt-Jakob disease, Gerstmann-Strassler Scheinker disease, bovine spongiform encephalopathy and the like) Alzheimer's disease, Parkinson's disease, Huntington's disease, type II diabetes, cystic fibrosis, emphysema, spinocerebellar ataxia, α-1-antitrypsin deficiency, and the like.

As noted above, certain aspects of the present invention relate to methods of treating a disease and/or disorder, or symptoms thereof (e.g., cytotoxicity), by selectively enhancing the degradation of a protein. In certain embodiments, the methods comprise administering a therapeutically effective amount of a pharmaceutical composition comprising a compound described herein to a subject (e.g., a mammal such as a human) in need thereof. Thus, one embodiment is a method of treating a subject suffering from or susceptible to a protein-expression related disease. In certain embodiments, the method includes the step of administering to the mammal a therapeutic amount of a compound herein sufficient to treat the disease or disorder, or symptom thereof, under conditions such that the disease or disorder is treated. In certain embodiments, the disease is selected from the group consisting of autosomal dominant retinitis pigmentosa, IMPDH1-mediated retinitis pigmentosa, chronic myelogenous leukemia, diabetes mellitus, cancer, Alzheimer's disease, a 1-antitrypsin deficiency, cystic fibrosis, nephrogenic diabetes insipidus, prion-mediated infections, age-related macular degeneration, Parkinson's disease, Huntington's disease, and intoxication with botulinum toxin.

In certain embodiments, administering a therapeutically effective amount of a pharmaceutical composition comprising a compound described herein which targets components of the circadian clock could be useful in treating, for example, sleep disorders and jet lag.

The methods herein include administering to the subject (including a subject identified as in need of such treatment) an effective amount of a compound described herein, or a composition described herein to produce a desired effect. Identifying a subject in need of such treatment can be in the judgment of the subject or a health care professional and can be subjective (e.g., opinion) or objective (e.g., measurable by a test or diagnostic method).

The therapeutic methods of the invention, which include prophylactic treatment, in general comprise administration of a therapeutically effective amount of at least one of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like).

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with protein-expression related disease (including misfolding), in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In certain embodiments, a second level of Marker in the subject is determined at a time point later than the determination of the first level, and the two levels are compared to monitor the course of disease or the efficacy of the therapy. In certain embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In another embodiment, the invention provides a method for utilizing a compound of the invention to investigate protein degradation.

In at least certain examples, the compounds disclosed herein can be used in the investigation of protein function. In certain embodiments, the method involves creating a fusion protein by attaching a protein with a known binding moiety to the protein of interest. In certain embodiments, the protein with a known binding moiety is GST, DHFR, SNAP, CLIP, or HALO. In certain embodiments, the fusion protein is contacted with any one of the aforementioned compounds.

Pharmaceutical Compositions

The present invention features pharmaceutical preparations comprising compounds together with pharmaceutically acceptable carriers, where the compounds provide for the selective degradation of a targeted protein. Such preparations have both therapeutic and prophylactic applications. Compounds of the invention may be administered as part of a pharmaceutical composition. The compositions and combinations of the invention can be part of a pharmaceutical pack, where each of the compounds is present in individual dosage amounts.

Pharmaceutical compositions of the invention to be used for prophylactic or therapeutic administration should be sterile. Sterility is readily accomplished by filtration through sterile filtration membranes (e.g., 0.2 µm membranes), by gamma irradiation, or any other suitable means known to those skilled in the art. Therapeutic polypeptide compositions generally are placed into a container having a sterile access port, for example, an intravenous solution bag or vial having a stopper pierceable by a hypodermic injection needle. These compositions ordinarily will be stored in unit or multi-dose containers, for example, sealed ampoules or vials, as an aqueous solution or as a lyophilized formulation for reconstitution.

The compounds may be combined, optionally, with a pharmaceutically acceptable excipient. The term "pharmaceutically-acceptable excipient" as used herein means one or more compatible solid or liquid filler, diluents or encapsulating substances that are suitable for administration into a human. The term "carrier" denotes an organic or inorganic ingredient, natural or synthetic, with which the active ingredient is combined to facilitate administration. The components of the pharmaceutical compositions also are capable of being co-mingled with the molecules of the present invention, and with each other, in a manner such that there is no interaction that would substantially impair the desired pharmaceutical efficacy.

The excipient often contains minor amounts of additives such as substances that enhance isotonicity and chemical stability. Such materials are non-toxic to recipients at the dosages and concentrations employed, and include buffers such as phosphate, citrate, succinate, acetate, lactate, tartrate, and other organic acids or their salts; tris-hydroxymethylaminomethane (TRIS), bicarbonate, carbonate, and other organic bases and their salts; antioxidants, such as ascorbic acid; low molecular weight (for example, less than about ten residues) polypeptides, e.g., polyarginine, polylysine, polyglutamate and polyaspartate; proteins, such as serum albumin, gelatin, or immunoglobulins; hydrophilic polymers, such as polyvinylpyrrolidone (PVP), polypropylene glycols (PPGs), and polyethylene glycols (PEGs); amino acids, such as glycine, glutamic acid, aspartic acid, histidine, lysine, or arginine; monosaccharides, disaccharides, and other carbohydrates including cellulose or its derivatives, glucose, mannose, sucrose, dextrins or sulfated carbohydrate derivatives, such as heparin, chondroitin sulfate or dextran sulfate; polyvalent metal ions, such as divalent metal ions including calcium ions, magnesium ions and manganese ions; chelating agents, such as ethylenediamine tetraacetic acid (EDTA); sugar alcohols, such as mannitol or sorbitol; counterions, such as sodium or ammonium; and/or nonionic surfactants, such as polysorbates or poloxamers. Other additives may be included, such as stabilizers, anti-microbials, inert gases, fluid and nutrient replenishers (i.e., Ringer's dextrose), electrolyte replenishers, and the like, which can be present in conventional amounts.

The compositions, as described above, can be administered in effective amounts. The effective amount will depend upon the mode of administration, the particular condition being treated and the desired outcome. It may also depend upon the stage of the condition, the age and physical condition of the subject, the nature of concurrent therapy, if any, and like factors well known to the medical practitioner. For therapeutic applications, it is that amount sufficient to achieve a medically desirable result.

With respect to a subject having a disease or disorder due at least in part to an excessive protein expression or expression of a mutant protein, an effective amount is sufficient to decrease the over-expressed or mutant protein in a cell, or an amount sufficient to stabilize, slow, or reduce the a symptom associated with a pathology. Generally, doses of the compounds of the present invention would be from about 0.01 mg/kg per day to about 1,000 mg/kg per day. In certain embodiments, doses ranging from about 50 to about 2000 mg/kg may be suitable. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of a composition of the present invention.

A variety of administration routes are available. The methods of the invention, generally speaking, may be practiced using any mode of administration that is medically acceptable, meaning any mode that produces effective levels of the active compounds without causing clinically unacceptable adverse effects. In one preferred embodiment, a composition of the invention is administered intraocularly. Other modes of administration include oral, rectal, topical, intraocular, buccal, intravaginal, intracisternal, intracerebroventricular, intratracheal, nasal, transdermal, within/on implants, or parenteral routes. The term "parenteral" includes subcutaneous, intrathecal, intravenous, intramuscular, intraperitoneal, or infusion. Compositions comprising a composition of the invention can be added to a physiological fluid, such as to the intravitreal humor. For CNS administration, a variety of techniques are available for promoting transfer of the therapeutic across the blood brain barrier including disruption by surgery or injection, drugs which transiently open adhesion contact between the CNS vasculature endothelial cells, and compounds that facilitate translocation through such cells. Oral administration can be preferred for prophylactic treatment because of the convenience to the patient as well as the dosing schedule.

Pharmaceutical compositions of the invention can comprise one or more pH buffering compounds to maintain the pH of the formulation at a predetermined level that reflects physiological pH, such as in the range of about 5.0 to about 8.0. The pH buffering compound used in the aqueous liquid formulation can be an amino acid or mixture of amino acids, such as histidine or a mixture of amino acids such as histidine and glycine. Alternatively, the pH buffering compound is preferably an agent which maintains the pH of the formulation at a predetermined level, such as in the range of about 5.0 to about 8.0, and which does not chelate calcium ions. Illustrative examples of such pH buffering compounds include, but are not limited to, imidazole and acetate ions. The pH buffering compound may be present in any amount suitable to maintain the pH of the formulation at a predetermined level.

Pharmaceutical compositions of the invention can also contain one or more osmotic modulating agents, i.e., a compound that modulates the osmotic properties (e.g, tonicity, osmolality and/or osmotic pressure) of the formulation to a level that is acceptable to the blood stream and blood cells of recipient individuals. The osmotic modulating agent can be an agent that does not chelate calcium ions. The osmotic modulating agent can be any compound known or available to those skilled in the art that modulates the osmotic properties of the formulation. One skilled in the art may empirically determine the suitability of a given osmotic modulating agent for use in the inventive formulation. Illustrative examples of suitable types of osmotic modulating agents include, but are not limited to: salts, such as sodium chloride and sodium acetate; sugars, such as sucrose, dextrose, and mannitol; amino acids, such as glycine; and mixtures of one or more of these agents and/or types of agents. The osmotic modulating agent(s) may be present in any concentration sufficient to modulate the osmotic properties of the formulation.

Compositions comprising a compound of the present invention can contain multivalent metal ions, such as calcium ions, magnesium ions and/or manganese ions. Any multivalent metal ion that helps stabilizes the composition and that will not adversely affect recipient individuals may be used. The skilled artisan, based on these two criteria, can determine suitable metal ions empirically and suitable sources of such metal ions are known, and include inorganic and organic salts.

Pharmaceutical compositions of the invention can also be a non-aqueous liquid formulation. Any suitable non-aqueous liquid may be employed, provided that it provides stability to the active agents (s) contained therein. Preferably, the non-aqueous liquid is a hydrophilic liquid. Illustrative examples of suitable non-aqueous liquids include: glycerol; dimethyl sulfoxide (DMSO); polydimethylsiloxane (PMS); ethylene glycols, such as ethylene glycol, diethylene glycol, triethylene glycol, polyethylene glycol ("PEG") 200, PEG 300, and PEG 400; and propylene glycols, such as dipropylene glycol, tripropylene glycol, polypropylene glycol ("PPG") 425, PPG 725, PPG 1000, PPG 2000, PPG 3000 and PPG 4000.

Pharmaceutical compositions of the invention can also be a mixed aqueous/non-aqueous liquid formulation. Any suitable non-aqueous liquid formulation, such as those described above, can be employed along with any aqueous liquid formulation, such as those described above, provided that the mixed aqueous/non-aqueous liquid formulation provides stability to the compound contained therein. Preferably, the non-aqueous liquid in such a formulation is a hydrophilic liquid. Illustrative examples of suitable non-aqueous liquids include: glycerol; DMSO; PMS; ethylene glycols, such as PEG 200, PEG 300, and PEG 400; and propylene glycols, such as PPG 425, PPG 725, PPG 1000, PPG 2000, PPG 3000 and PPG 4000.

Other delivery systems can include time-release, delayed release or sustained release delivery systems. Such systems can avoid repeated administrations of compositions of the invention, increasing convenience to the subject and the physician. Many types of release delivery systems are available and known to those of ordinary skill in the art. They include polymer base systems such as polylactides (U.S. Pat. No. 3,773,919 (incorporated by reference); European Patent No. 58,481), poly(lactide-glycolide), copolyoxalates, polycaprolactones, polyesteramides, polyorthoesters, polyhydroxybutyric acids, such as poly-D-(−)-3-hydroxybutyric acid (European Patent No. 133, 988), copolymers of L-glutamic acid and gamma-ethyl-L-glutamate (Sidman, K. R. et al., Biopolymers 22: 547-556), poly (2-hydroxyethyl methacrylate) or ethylene vinyl acetate (Langer, R. et al., J. Biomed. Mater. Res. 15:267-277; Langer, R. Chem. Tech. 12:98-105), and polyanhydrides.

Other examples of sustained-release compositions include semi-permeable polymer matrices in the form of shaped articles, e.g., films, or microcapsules. Delivery systems also include non-polymer systems that are: lipids including sterols such as cholesterol, cholesterol esters and fatty acids or neutral fats such as mono- di- and tri-glycerides; hydrogel release systems such as biologically-derived bioresorbable hydrogel (i.e., chitin hydrogels or chitosan hydrogels); sylastic systems; peptide based systems; wax coatings; compressed tablets using conventional binders and excipients; partially fused implants; and the like. Specific examples include, but are not limited to: (a) erosional systems in which the agent is contained in a form within a matrix such as those described in U.S. Pat. Nos. 4,452,775, 4,667,014, 4,748,034 and 5,239,660 (all four are incorporated by reference) and (b) diffusional systems in which an active component permeates at a controlled rate from a polymer such as described in U.S. Pat. Nos. 3,832,253, and 3,854,480 (both are incorporated by reference).

Another type of delivery system that can be used with the methods and compositions of the invention is a colloidal dispersion system. Colloidal dispersion systems include lipid-based systems including oil-in-water emulsions, micelles, mixed micelles, and liposomes. Liposomes are artificial membrane vessels, which are useful as a delivery vector in vivo or in vitro. Large unilamellar vessels (LUV), which range in size from 0.2-4.0 μm, can encapsulate large macromolecules within the aqueous interior and be delivered to cells in a biologically active form (Fraley, R., and Papahadjopoulos, D., Trends Biochem. Sci. 6: 77-80).

Liposomes can be targeted to a particular tissue by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2,3 dioleyloxy)-propyl]-N, N,N-trimethylammonium chloride (DOTMA) and dimethyl dioctadecylammonium bromide (DDRB). Methods for making liposomes are well known in the art and have been described in many publications, for example, in DE 3,218, 121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. No. 4,485,045 (incorporated by reference) and U.S. Pat. No. 4,544,545 (incorporated by reference); and EP 102,324. Liposomes also have been reviewed by Gregoriadis, G., Trends Biotechnol., 3: 235-241).

Another type of vehicle is a biocompatible microparticle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System"). PCT/US/0307 describes biocompatible, preferably biodegradable polymeric matrices for containing an exogenous gene under the control of an appropriate promoter. The polymeric matrices can be used to achieve sustained release of the exogenous gene or gene product in the subject.

The polymeric matrix preferably is in the form of a microparticle such as a microsphere (where an agent is dispersed throughout a solid polymeric matrix) or a microcapsule (where an agent is stored in the core of a polymeric shell). Microcapsules of the foregoing polymers containing drugs are described in, for example, U.S. Pat. No. 5,075,109 (incorporated by reference). Other forms of the polymeric matrix for containing an agent include films, coatings, gels, implants, and stents. The size and composition of the polymeric matrix device is selected to result in favorable release kinetics in the tissue into which the matrix is introduced. The size of the polymeric matrix further is selected according to the method of delivery that is to be used. Preferably, when an aerosol route is used the polymeric matrix and composition are encompassed in a surfactant vehicle. The polymeric matrix composition can be selected to have both favorable degradation rates and also to be formed of a material, which is a bioadhesive, to further increase the effectiveness of transfer. The matrix composition also can be selected not to degrade, but rather to release by diffusion over an extended period of time. The delivery system can also be a biocompatible microsphere that is suitable for local, site-specific delivery. Such microspheres are disclosed in Chickering, D. E., et al., Biotechnol. Bioeng., 52: 96-101; Mathiowitz, E., et al., Nature 386: 410-414.

Both non-biodegradable and biodegradable polymeric matrices can be used to deliver the compositions of the invention to the subject. Such polymers may be natural or synthetic polymers. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

Exemplary synthetic polymers which can be used to form the biodegradable delivery system include: polyamides, polycarbonates, polyalkylenes, polyalkylene glycols, polyalkylene oxides, polyalkylene terephthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly (methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly(ortho)esters, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Kits

The invention further provides kits for the treatment or prevention of diseases that are due at least in part to excessive protein expression or expression of a mutant protein, or the symptoms thereof. In one embodiment, the kit includes a pharmaceutical pack comprising an effective amount of a composition comprising a compound of the invention. Typically, the compositions are present in unit dosage form. In some embodiments, the kit comprises a sterile container which contains a therapeutic or prophylactic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, compositions of the invention or combinations thereof are provided together with instructions for administering them to a subject having or at risk of developing a disease that is due at least in part to excessive protein expression or expression of a mutant protein. The instructions will generally include information about the use of the compounds for the treatment or prevention of said diseases. In other embodiments, the instructions include at least one of the following: description of the compound or combination of compounds; dosage schedule and administration for treatment of a disease that is due at least in part to excessive protein expression or expression of a mutant protein, or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

EXEMPLIFICATION

The invention now being generally described, it will be more readily understood by reference to the following, which is included merely for purposes of illustration of certain aspects and embodiments of the present invention, and is not intended to limit the invention.

All reagents were from Sigma Aldrich chemical company unless otherwise stated and were used without further purification. All solvents were of HPLC grade. Thin layer chromatography was performed on commercial glass backed plates SiliaPlate G (Silicycle®). These were visualized using UV illumination or iodine, permanganate or ceric ammonium nitrate stains. Chromatography was performed on either Siliflash F60 (silicycle) or basic alumina (Sigma Aldrich). All glassware was flame-dried and cooled in vacuo prior to use. All reactions were carried out under an atmosphere of dry nitrogen using magnetic stirring. 1-Ethyl-3-(3-dimethylaminopropyl)carbodiimide was from ChemImpex®. Centrifugation was carried out on an Eppendorf® centrifuge 5417C. Anti hemagglutinin (YPYDVPDYA) antibody conjugated to horseradish peroxidase (anti-HA-HRP) was from Roche diagnostics (monoclonal from rat, clone 3F10). Polyclonal anti-GST-α1 and anti-GST-π were from Oxford Biomedical. Anti-glyceraldehyde-3-phosphate dehydrogenase conjugated to horseradish peroxidase (anti-GAPDH-HRP) was from Aldrich. Trypsin, Dulbecco's Modified Minimal Essential Medium, 100× penicillin (10000 units/mL)/streptomycin 10 mg/mL, 100×L-glutamine (200 mM), 0.25% trypsin and phosphate buffered saline were from Gibco®. 20S Proteasome and immunoproteasome were from Boston Biochem. Loading buffer was of the following composition: 250 mM Tris, pH 6.8, 10% sodium dodecyl sulfate, 30% glycerol, 0.02% bromophenol blue, 150 mM dithiothreitol. $^1$H NMR spectra were recorded on a Brucker 400 spectrometer and are reported in ppm (parts per million) with reference to an internal standard (CDCl$_3$ at 7.26 ppm). Data are reported as [integration, s=singlet, d=doublet, t=triplet, q=quartet, m=multiplet, coupling constant(s) in Hz].

Example 1—General Procedure for Peptide Coupling Reactions

The acid, amine, 1-ethyl-3-(3-dimethylaminopropyl)carbodiimide, and triethylamine were dissolved in dimethylformamide and stirred overnight. The volatiles were removed in vacuo and the residue redissolved in chloroform and washed successively with 10% citric acid, sodium bicarbonate, and water. The chloroform phase was dried with magnesium sulfate, filtered and concentrated in vacuo to give the crude product.

Example 2—General Procedure for Western Blotting

The gel was transferred onto a polyvinyldifluoride membrane in Towbin (3 g Tris/14.4 g glycine) buffer, 100V for 1.2 hours then 40V for 3 hours for 18% gels, and 100 V for 1.2 hours for 12% gels. The membrane was blocked with 3% non-fat milk in Tris buffered saline (100 mM Tris base, 500 mM NaCl, pH 7.6) for one hour, then directly added to a solution of anti HA-HRP conjugated antibody in 0.5% non-fat milk in Tris buffered saline with 0.05% tween-20 for 2 hours. Membrane was washed twice with Tris buffered saline with 0.05% Tween 20 for 10 minutes, then washed once with Tris buffered saline for 15 minutes. The residual buffer was removed then exposed to ECL Plus™ (GE healthcare) for 5 minutes. Membrane was visualized by exposure to film (HyBlot CL, Denville Scientific). For in cell degradation assays, the membrane was cut in half (at approximately 40 kiloDaltons) and the lower molecular weight portion was probed and visualized with anti-GAPDH-HRP, protocol same as for anti-HA except Tris buffered saline contained 150 mM NaCl, not 500 mM. The higher molecular weight portion of the membrane was probed and visualized with anti-HA-HRP.

Example 3—Preparation of Selected Compounds

Selected compounds are shown in FIG. 1; the preparation of some of these compounds is detailed below. Some of the reactions detailed are based on Calloway, N. T.; Choob, M.; Sanz, A.; Sheetz, M. P.; Miller, L. W.; Cornish, V. W. *ChemBioChem* 2007, 8, 767-774.

N-(6-Aminohexyl)-5-(2,3-di-t-butoxycarbonylguanidino)-2-(t-butoxycarbonylamino)pentanamide (8)

To a mixture of 1,6-hexanediamine 3 (857 mg, 7.35 mmol) and 1-ethyl-3-(3-dimethylaminopropyl)carbodiimide (326 mg, 2.10 mmol) in DMF (200 mL) was added ω,ω', α-N-tri-t-boc arginine 6 (500 mg, 1.05 mmol) (ChemImpex®) in dimethylformamide (200 mL) via cannula. The resulting mixture was stirred overnight. The dimethylformamide was removed in vacuo and the resulting solid redissolved in chloroform (50 mL), washed successively with saturated sodium carbonate and water and then dried with magnesium sulphate and concentrated in vacuo. The mixture was purified by basic alumina chromatography to yield the title compound (210 mg, 35%) as a white solid.

N-(6-(2-(2,3-Dichloro-4-(2-methylenebutanoyl)phenoxy)acetamido)hexyl)-5-(2,3-di-t-butoxycarbonylguanidino)-2-(t-butoxycarbonylamino)pentanamide (1)

Following Example 1: free amine 8 (200 mg, 0.35 mmol), 1-ethyl-3-(3-dimethylaminopropyl)carbodiimide (105 mg, 0.70 mmol), ethacrynic acid 5 (121 mg, 0.40 mmol) and triethylamine (48 µL, 0.35 mmol) were dissolved in dimethylformamide (10 mL). The crude product was purified by silica gel chromatography (hexane to ethyl acetate step gradient 10% increments) to afford the title compound (214 mg, 50%) as an off white solid. $\delta_H$ (400 MHz, CDCl$_3$) 1.10 (3H, t, J=6.8), 1.19-1.71 (12H, m), 1.40 (9H, s), 1.45 (9H, s), 1.47 (9H, s), 2.42 (2H, q, J=6.8), 3.12 (1H, m), 3.25 (1H, m), 3.31 (2H, t, J=8.1), 3.64 (1H, m), 3.93 (1H, m), 4.22 (1H, s), 4.53 (2H, s), 5.55 (1H, s), 5.92 (1H, s), 6.82 (1H, d, J=7.2), 7.15 (1H, d, J=7.2).

N-(6-Trifluoroacetylaminohexyl)-2-(benzylcarbonyloxyamino)-5-(3-tosylguanidino)pentanamide (11)

Following Example 1: free amine 4 (200 mg, 0.35 mmol), 1-ethyl-3-(3-dimethylaminopropyl)carbodiimide (105 mg, 0.94 mmol), ethacrynic acid 5 (285 mg, 0.94 mmol) and triethylamine (96 µL, 0.70 mmol) were dissolved in DMF (5 mL). The crude product was purified by silica gel chromatography (hexane to ethyl acetate step gradient 20% increments) to afford the title compound (137 mg, 60%) as an off white solid.

N-(6-Aminohexyl)-2-(benzylcarbonyloxyamino)-5-(3-tosylguanidino)pentanamide (9)

Trifluoroacetamide 11 (137 mg, 0.21 mmol) was treated with LiOH (25 mg, 1.05 mmol) in methanol with 3% water (5 mL) overnight. Volatiles were removed in vacuo and the crude product was used without purification.

N-(6-(2-(2,3-Dichloro-4-(2-methylenebutanoyl)phenoxy)acetamido)hexyl)-2-(benzylcarbonyloxyamino)-5-(3-tosylguanidino)pentanamide (2)

Following Example 1: free amine 9 (100 mg, 0.18 mmol), 1-ethyl-3-(3-dimethylaminopropyl)carbodiimide (41 mg, 0.36 mmol), ethacrynic acid 5 (54 mg, 0.18 mmol) and triethylamine (48 µL, 0.35 mmol) were dissolved in DMF (5 mL). Purification by chromatography on silica gel (50% ethyl acetate in hexane to 10% methanol in ethyl acetate) gave the title compound (58 mg, 36%) as a white solid. $\delta_H$ (400 MHz, CDCl$_3$) 1.11 (3H, t, J=6.8), 1.20-1.85 (12H, m), 2.38 (3H, s), 2.45 (2H, q, J=6.8), 3.16-3.40 (6H, m), 4.28 (1H, q, J=3.2), 4.57 (2H, s), 5.19 (2H, s). 5.60 (1H, s), 5.85 (1H, d, J=8.0), 5.95 (1H, s), 6.30 (2H, br s), 6.83 (2H, overlapping), 7.18 (1H, d, J=7.3), 7.21 (2H, d, J=5.4), 7.28-7.35 (5H, m) 7.76 (2H, d, J=5.4).

4-((2,4-Diaminopyrimidin-5-yl)methyl)-2,6-dimethoxyphenol (13)

Trimethoprim 12 (10 g, 34.48 mmol) (Chem Impex®) was dissolved in 48% aqueous HBr (125 mL) and refluxed for 20 minutes. 50% aqueous NaOH (30 mL) was then added and the resulting solution cooled to 4° C. overnight to give the crude product as beige crystals. These crystals were dissolved in the minimum amount of 90° C. water and allowed to precipitate at room temperature, the liquid phase removed, and the solid dried in a lyophilizer to yield the title compound as a white solid (5.23 g, 55%).

Methyl 2-(4-((2,4-diaminopyrimidin-5-yl)methyl)-2,6-dimethoxyphenoxy)acetate (14)

Compound 13 (500 mg, 1.81 mmol) in dimethylformamide was treated with NaH (60% dispersion in mineral oil) (76 mg, 1.90 mmol) to form a red colored mixture. To this was added methyl bromoacetate (275 mg, 1.81 mmol) and the reaction mixture stirred for 30 minutes. The volatiles were removed in vacuo (caution! Methyl bromoacetate is toxic and should be used in a fume hood at all times). The crude reaction product was used without further purification.

2-(4-((2,4-diaminopyrimidin-5-yl)methyl)-2,6-dimethoxyphenoxy)acetic acid (15)

Ester 14 (400 mg, 1.15 mmol) was dissolved in methanol and 3% water (5 mL) and to it was added LiOH (83 mg, 3.45 mmol). The mixture was stirred for 4 hours and then concentrated in vacuo. The residue was redissolved in the minimum of water and the pH lowered to 3 by the addition of HCl. The precipitate was filtered and lyophilized to give the title compound as a white solid (300 mg, 80%).

N-(6-aminohexyl)-2-(4-((2,4-diaminopyrimidin-5-yl)methyl)-2,6-dimethoxyphenoxy)acetamide (16)

Following Example 1: acid 15 (500 mg, 1.50 mmol), 1-Ethyl-3-(3-dimethylaminopropyl)carbodiimide (460 mg, 3.00 mmol), triethyl amine (209 mL, 1.65 mmol), and mono t-Boc 1,6-hexanediamine (356 mg, 1.54 mmol) in dimethylformamide (5 mL) were reacted. However, after stirring overnight, t-Boc$_2$O (2.25 g, 10.5 mmol) was added and the mixture was stirred for a further 24 hours. This was then concentrated in vacuo and purified by silica gel chromatography to give the crude product which was purified by chromatography on silica gel (3% methanol in ethyl acetate). This was treated with 1:1 trifluoroacetic acid: dichloromethane (10 mL) and stirred for 1 hour. The volatiles were removed in vacuo to give the crude product which was used without further purification (250 mg, 40%). $\delta_H$ (400 MHz, CD$_3$SOCD$_3$) 1.00-1.33 (4H, m), 1.38-1.41 (4H, m), 2.73 (2H, t, J=5.1 Hz), 3.00 (2H, m), 3.54 (2H, s), 3.72 (6H, s), 4.21 (2H, s), 6.62 (2H, s), 7.18 (2H, br s), 7.42 (1H, s).

N-(6-(2-(4-((2,4-diaminopyrimidin-5-yl)methyl)-2,6-dimethoxyphenoxy)acetamido)hexyl)-5-(2,3-di-t-butoxycarbonylguanidino)-2-(t-butoxycarbonylamino)pentanamide (22)

Following Example 1: free amine 16 (100 mg, 0.23 mmol), 1-benzotriazol-1-yl-oxytripyrrolidinophosphonium hexafluorophosphate (240 mg, 0.46 mmol), tri-t-bocarginine (118 mg, 0.25 mmol) and triethylamine (33 pt, 0.25 mmol) in dimethylformamide (4 mL) were reacted together. The crude product was purified by silica gel chromatography and then recrystallized from hot chloroform to yield the title compound as a solid. $\delta_H$ (400 MHz, $CD_3SOCD_3$) 1.13-1.20 (6H, m), 1.25 (9H, s), 1.30 (9H, s), 1.40 (9H, s), 1.20-1.45 (6H, m), 2.90-3.10 (2H, m), 3.10 (2H, q, J=3.2 Hz), 3.50 (2H, s), 3.72 (6H, s), 3.70-3.82 (3H, m), 4.18 (2H, s), 6.02 (2H, br s) 6.45 (2H, br s), 6.60 (2H, s), 6.78 (1H, s), 7.44 (1H, s), 7.75 (1H, s), 7.87 (1H, s), 9.05 (2H, br s).

5-(2,3-Di-tert-butoxycarbonylguanidino)-2-(tert-butoxycarbonylamino)-N-(6-(tritylthio)hexyl)pentanamide (18)

Following Example 1: amine 17 (1.00 g, 2.67 mmol), 1-ethyl-3-(3-dimethylaminopropyl)carbodiimide (820 mg, 5.34 mmol), 6 (1.26 g, 2.67 mmol), and triethylamine (375 μL, 2.67 mmol) were reacted to give the title compound. This was used from crude.

6-(5-(2,3-Di-tert-butoxycarbonylguanidino)-2-(di-tert-butoxyamino)pentanamido)hexyl ethanethioate (19)

Compound 18 (1 g, 1.71 mmol), was treated with $I_2$ (0.88 g, 3.42 mmol) in MeCN (10 mL)/water (1 mL). The crude product was treated with $PPh_3$ (1.79 g, 6.84 mmol)/water (1 mL) in tetrahydrofuran (10 mL) for 5 hours and then treated directly with excess acetyl chloride. Chromatography on silica (10% ethyl acetate in hexane to 100% ethyl acetate) gave the title compound (127 mg, 20%). $\delta_H$ (400 MHz, $CDCl_3$) 1.23-1.78 (12H, m), 1.42 (9H, s), 1.44 (9H, s), 1.49 (9H, s), 2.21 (3H, s), 2.80 (2H, t, J=7.1), 3.12 (1H, m), 3.28 (1H, m), 3.64 (1H, m), 3.96 (1H, m), 4.25 (1H, m) 5.93 (1H, d, J=5.5), 6.92 (1H, m), 9.25 (1H, br s), 9.38 (1H, br s).

5-(2,3-Di-tert-butoxycarbonylguanidino)-2-(tert-butoxycarbonylamino)-N-(6-(7-nitrobenzo[c][1,2,5]oxadiazol-4-ylthio)hexyl)pentan amide (20)

Compound 19 (127 mg, 0.34 mmol) was dissolved in degassed phosphate buffer pH 7.8 (20 mL) and to it was added 21 (60 mg, 0.30 mmol). The resulting solid was recrystallized three times from hot ethyl acetate to give the pure compound. $\delta_H$ (400 MHz, $CDCl_3$) 1.20-1.90 (12H, m), 1.40 (9H, s), 1.44 (9H, s), 1.50 (9H, s), 3.15 (1H, m), 3.20 (2H, t, J=6.5), 3.32 (1H, m), 3.65 (1H, m), 3.94 (1H, m), 4.23 (1H, m), 5.95 (1H, m), 6.95 (1H, m), 7.10 (1H, d, J=6.0), 8.38 (1H, d, J=6.0), 9.21 (1H, s), 9.33 (1H, s).

Example 4—Preparation of Human Glutathione-S-Transferase α-1 Bearing a Tag

Human glutathione-S-transferase α-1 bearing an N-terminal HA tag was recombinantly expressed in *Escherichia coli* using the pOXO4-α1 vector. This was purified using glutathione affinity chromatography (GST-Bind™, Novagen). *Escherichia coli* dihydrofolate reductase bearing an N-terminal $(His)_6$ tag and a C-terminal HA tag was recombinantly expressed in *Escherichia coli* using a pET28a vector. This was purified using Ni-NTA resin (Qiagen).

Example 5—Degradation of a Pre-Inhibited Protein in a Cell Lysate

All cells were grown in Dulbecco's Modified Minimal Essential Medium supplemented with 10% fetal bovine serum, 1×L-glutamine and 1× penicillin/streptomycin (complete medium) to 90% confluence. The cells were then serum starved for 2 days in the case of Cos and HeLa cells and 1 day in the case of NIH3T3 cells. The cells were washed with phosphate buffered saline and then trypsinized. Cells were collected, and an equal volume of complete medium was added. Cells were pelleted by centrifugation and the supernatant was aspirated. The cell pellet was washed three times with phosphate buffered saline. Cell pellets were stored at −80° C. until required. Cells were thawed on ice and maintained at 4° C. until required for the assay. Cells were then resuspended in ice cold lysis buffer (150 mM sucrose, 200 mM sodium phosphate, 43 mM $MgCl_2$, pH 7.8). The cells were lysed in a Dounce homogenizer (10 strokes), and then centrifuged at 14000 rpm for 30 minutes. The clarified lysate was normalized to an optimized concentration of 1 mg/mL (Bradford assay, Biorad®, as per manufacturer's instructions, using immunoglobulin as a standard) with lysis buffer. A 10×ATP regeneration buffer was made consisting of the following 1 mg/mL creatine kinase (Roche Diagnostics®), 600 mM creatine phosphate, 100 mM ATP, 200 mM Tris pH 8.0, 600 mM $MgCl_2$. This was incubated at 37° C. for 30 minutes prior to use. Assays were conducted in 55 pit total volume [including 1×ATP regeneration buffer, and 120 ng of HA-tagged protein (1 μL) preinhibited with 100 μM ethacrynic acid-derived inhibitor, or 1 μM trimethoprim-derived inhibitor] in 250 μL PCR tubes. Prior to assay 50 μL Chill Out wax (Biorad®) was overlaid on the top of the vial. 15 μL aliquots were extracted and diluted into 6 μL of 5× reducing SDS PAGE loading buffer and immediately frozen by being placed into dry ice. These were stored at −80° C. until required. Samples were thawed at 100° C. and continued to be boiled for 5 minutes. The samples were then centrifuged at 14,000 rpm on a microcentrifuge for 30 minutes and loaded onto an 18% polyacrylamide SDS PAGE gel, and Western blotted as per Example 2.

Example 6—In Cell Degradation Assays

Cells were grown to 90% confluence in Dulbecco's Modified Minimal Essential Medium supplemented with 10% fetal bovine serum, 1×L-glutamine with no antibiotic in a 6 well plate. At this point the cells were serum starved, and then transfected using 1 pig plasmid (expression driven by the cytomegalovirus promoter; gene coding for enhanced green fluorescent protein fused to the C-terminus of *E. coli* dihydrofolate reductase): 2 μL Transfectin™ (Biorad) per well. 48 hours after transfection, media was once again aspirated, and fresh serum free media was added. Cycloheximide (final concentration 100 μg/mL) was then added to the cells and after 5 minutes, 30 μM inhibitor was added. At each time point (45 minutes), media was aspirated, cells were trypsinized, centrifuged and washed three times with phosphate buffered saline. Cell pellets were flash frozen in dry ice, and then stored indefinitely at −80° C. The cells were thawed on ice, and then resuspended in lysis buffer (150 mM sucrose, 200 mM sodium phosphate, 43 mM MgCl$_2$, pH 7.8, 0.1% triton X-100). Cells were lysed by two freeze/thaw cycles (−80° C. for 5 minutes, then 4° C. for 10 minutes). Lysate concentrations were normalized by dilution with lysis buffer such that they gave the same A$_{595}$ when diluted into Bradford assay dye (Biorad). Equal volumes of normalized lysate were resolved on a 12% SDS PAGE gel and blotted as indicated in Example 2.

Example 7—Degradation by Purified 20S Proteasome

The protein was pre-inhibited with 1 mM inhibitor by incubation at 30° C. for 20 minutes. This mixture was added to the assay mixture (in 50 mM Hepes, pH 8.0, 250 mM NaCl, 1 mM DTT) such that the final concentration of protein was 90 nM. The concentration of proteasome was 6 nM. The temperature of assay was 37° C. Total assay volume was 55 μL. 15 μL aliquots were extracted at various time points and immediately placed into 6 μL of 5× loading buffer and boiled for 5 minutes. These were stored at −80° C. after flash freezing on dry ice and thawed by boiling for 2 minutes. The data was analyzed by Western blot as described in Example 2.

Example 8—Structure-Activity Relationship (SAR) for Boc$_3$Arg-Induced Protein Degradation SAR of the Boc$_3$Arg Moiety.

We will systematically vary the structure of Boc$_3$Arg to determine the minimum requirements for degradation. We will also investigate the length, flexibility and chemical composition of the ligand to determine the role of the linker in the degradation process.

Figure 14:
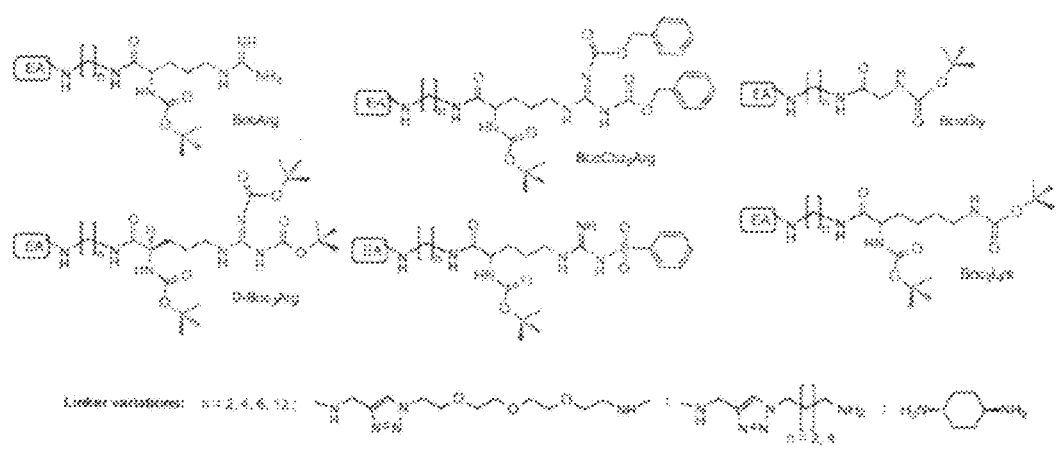
FIG. 14 depicts various potential Boc$_3$Arg-linker derivatives. L-Amino acids will be used unless otherwise noted.

We will use the GST-α-1/EA system for these experiments because the synthesis of these compounds is more facile than derivatives of either Fur or TMP. Initial SAR will utilize commonly available protected amino acids. FIG. 14 shows a selection of the first compounds that will be tested. The syntheses are straightforward from readily available precursors—well within the synthetic expertise of my laboratory. If the triazole linker is active, we will be able to use copper-assisted alkyne azide cycloaddition (a/k/a as CLICK chemistry) to synthesize rapidly a wide variety of derivatives.

We will initially assay degradation by adding recombinant GST-α-1 to Hela cell lysates. Compounds that are active in this assay will be tested for the ability to degrade the GST-α-1-GFP in whole cells using the global protein stability assay. We will use a smaller set of compounds to determine if the same SAR is found in the TMP/eDHFR system, and expand on this set as necessary.

These experiments will define the minimum chemical moiety that can induce degradation. This information is critical for future applications—the smaller the destabilizer moiety, the more likely the eventual compound is to be biocompatible and bioavailable. Boc$_3$Arg alone has a molecular weight of 473 Da, so any ligand-linker-Boc$_3$Arg compound will be much bigger than generally recommended for drug-like molecules. Therefore, reducing the size of the destabilizing moiety will be important for eventual therapeutic applications. However, even if the current Boc$_3$Arg-linker proves to be the only functionality that can induce degradation, the preliminary results suggest that Boc$_3$Arg-induced degradation can be a useful tool. We note that similarly large molecules are used in imaging applications.

This information will also provide important insights into the mechanism of degradation. For example, if degradation results simply from exposed hydrophobic surface, then many different functionalities will be active. In contrast, if degradation results from a specific interaction between Boc$_3$Arg and a cellular factor such as the 20S proteasome, then very defined SAR should emerge. Alternatively, if the Boc$_3$Arg tag must intercalate into the structure of the target protein, then the length and flexibility of the linker region will be critical.

We expect that similar SAR will be observed in both EA/GST and TMP/eDHFR systems. We will test this assumption early in the SAR studies—should this prove not to be the case, we will focus on the SAR of the TMP/eDHFR system, since this system is more likely to develop into a general system for protein knockdown.

Relationship Between Affinity/Dissociation Rate of the Target-Inhibitor Interaction and Degradation.

Figure 15:
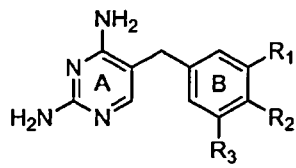
FIG. 15 depicts a SAR profile of TMP. These compounds may be used to determine the affinity requirements of the recognition ligand. R$_2$ will be the Boc$_3$Arg-linker. pK$_i$, –log K$_i$ projected based on published SAR of TMP.

The requirements of the target-inhibitor interaction must be defined so that this methodology can be readily applied to other protein targets. While TMP demonstrates that a noncovalent recognition element can be used to target a protein for degradation, the affinity of TMP for eDHFR is very high (<1 nM) and the dissociation rate is very slow (k$_{off}$ is <0.0005 s$^{-1}$). Lower affinity recognition ligands are likely to be less effective. These experiments take advantage of the well-described SAR of TMP. The compounds shown in FIG. 15 are expected to differ in affinity by a factor of 10$^3$. The syntheses of these compounds will follow published procedures. Degradation will be monitored in cell lysates and whole cells as described above.

We will determine the affinity and kinetics of inhibitor binding as previously described. These experiments are more challenging than typically encountered in ligand binding because TMP is a slow binding inhibitor. TMP affinity is buffer dependent, and also depends on the presence of cofactor NADPH/NADP$^+$. We will use a combination of progress curve analysis, stopped flow fluorescence, and displacement of $^{14}$C-TMP (Moravek) as appropriate to monitor the affinity and kinetics of inhibitor binding.

These experiments will establish the lower limit of binding affinity for the recognition element. This information is required for the selection of recognition elements for new protein targets. We may need to characterize more compounds if the affinity does not behave as expected. Another potential complication is that the rate of dissociation may be a more critical parameter than simple affinity. Again, it may require the characterization of more compounds to delineate the critical properties of the recognition ligand.

Generality of the Degradation/Destabilization Activities with Respect to Protein Targets.

We have demonstrated that Boc$_3$Arg induces degradation in the context of three different ligands and three different proteins. We will expand this set to three additional ligand/protein pairs, and also determine how cellular localization affects the degradation of eDFR fusion proteins.

BG/SNAP.

The SNAP tag was developed from the DNA repair protein O$^6$-alkylguanine-DNA alkyltransferase. SNAP is a 20 kDa protein; it reacts with benzylguanine (BG) derivatives to form a covalent adduct. BG can be modified as indicated with dyes and other probes using readily accessible synthetic methods. This system has been used to specifically label fusion proteins in vivo. We will purify recombinant SNAP-GFP fusion proteins to test degradation in Hela cell lysates and express SNAP-GFP in Hela cells for use in the global protein stability assay.

BC/CLIP.

The CLIP tag is a derivative of SNAP that reacts with O2-benzylcytosine (BC) derivatives. Importantly, SNAP and CLIP can be used simultaneously.

DS/Bcr-Abl.

Bcr-Abl is the aberrant protein kinase formed in the gene fusion event that is responsible for chronic myelogenous leukemia (CML). Selective Bcr-Abl inhibitors such as imatinib mesylate (i.e., Gleevec®) have been very successful in treating CML. Nonetheless, new therapies are needed to combat resistance. Importantly, simply blocking the kinase activity of the Bcr-Abl kinase is not sufficient to block activation of all its downstream signaling pathways; obviously such kinase activity-independent signaling would be eliminated if Bcr-Abl was degraded. Further, neither imatinib nor the second generation inhibitor dasatinib (DS) induce apoptosis of CML stem cells. This failure to eliminate CML stem cells is believed to cause relapse when drug is withdrawn. Perhaps degradation of Bcr-Abl will eliminate CML stem cells.

Figure 16:
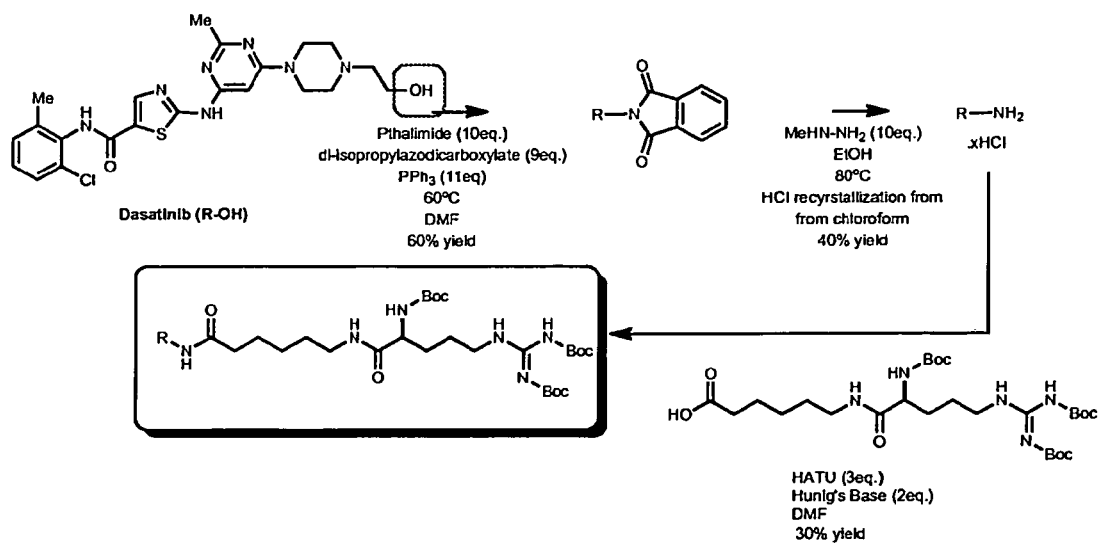
FIG. 16 depicts a proposed synthesis of DS-Boc$_3$Arg.

DS can be modified at the pendant hydroxyl group with little effect on its inhibition properties (FIG. 16). We will synthesize DS-Boc$_3$Arg as shown in FIG. 16. We will express Bcr-Abl in NIH3T3 cells using an MSCV vector system. Briefly, this vector will be transcribed into Bosc23 cells, which produce an mRNA containing 5'LTR-Bcr-Abl-IRES-GFP-3'LTR, expressing the p210 form of Bcr-Abl and GFP. This mRNA will be packaged into retroviral capsids by the Bosc23 cells. This virus will be used to transfect NIH3T3 cells. Transfected cells will be isolated by cell sorting based on GFP expression. Bcr-Abl expression will be confirmed by immunoblotting with commercially available antibodies. DS also inhibits Src family kinases, so we will also monitor the degradation of these endogenous proteins by immunoblotting with commercially available antibodies. If degradation is observed, we will compare the dose-dependence of DS and DS-Boc$_3$Arg inhibition of Bcr-Abl and Src signaling pathways. We will use anti-phospho-Tyr antibodies to assess overall Tyr kinase activity, anti-Src-phosphoTyr416 to assess Src activation (Src activation proceeds in the presence of imatinib but is blocked by DS) and anti-phospho-CrkL (CrkL phosphorylation is blocked by both imatinib and DS). These antibodies are commercially available from Santa Cruz Biotechnology and Cell Signaling Technology.

Determination of the Localization Constraints on Boc$_3$Arg-Induced Degradation.

Figure 17:
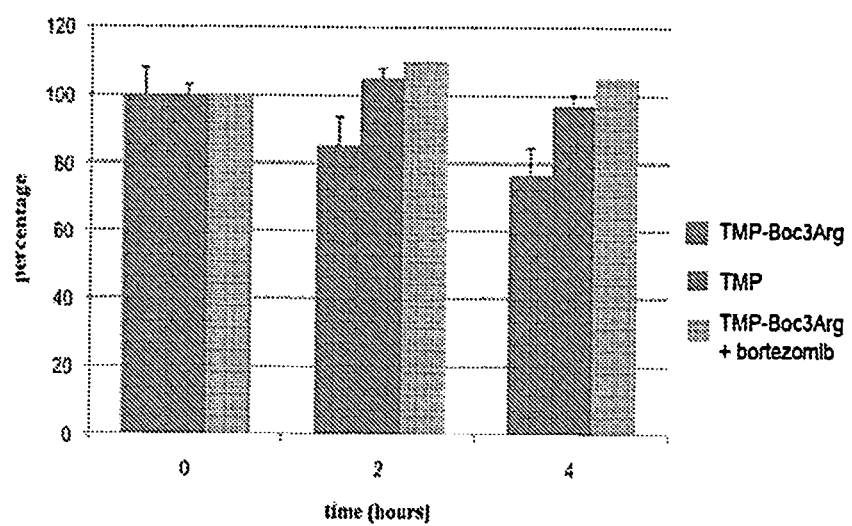
FIG. 17 depicts the degradation of eDHFR-HA by purified 20S proteasome.

The preliminary and above experiments have test the degradation of cytosolic proteins. We will further test the repertoire of Boc$_3$Arg-induced degradation by determining if the TMP/eDHFR system can degrade membrane-associated proteins, nuclear proteins and organelle-localized proteins. For example, FIG. 17 shows that TMP-Boc$_3$Arg can induce the degradation of a K-Ras-eDHFR fusion protein, suggesting that this method can effectively knockdown membrane associated proteins. Ras mutations are a common cause of cancer, so these experiments will also demonstrate the potential of degradation as a strategy for cancer chemotherapy.

Identification of Organisms Susceptible to Boc$_3$Arg-Induced Degradation.

Our preliminary results demonstrate that Boc$_3$Arg induces degradation in a wide variety of mammalian tissue culture cells. We will further test the operational range in commonly used model organisms *E. coli, Saccharomyces cerevisiae, Drosophila melanogaster* (S2 cells), and *Toxoplasma gondii*. We will use the EA/GST for initial experiments in lysates. If Boc$_3$Arg induced degradation is observed, we will express eDHFR-GFP fusion proteins and determine if TMP-Boc$_3$Arg can induce degradation in whole cells.

These experiments will determine the spectrum of organisms that are amenable to Boc$_3$Arg-induced protein knockdown. One potential pitfall is that TMP-Boc$_3$Arg may not be permeable in some of these systems. We will test this by comparing eDHFR-GFP degradation in lysates and/or permeabilized cells. The organism spectrum will also provide important clues to the mechanism of Boc$_3$Arg-induced degradation.

Example 9—Elucidation of the Mechanism of Boc$_3$Arg-Induced Degradation

These experiments will help to identify the cellular components that are required for Boc$_3$Arg-induced degradation. Three models are proposed.

Model 1: The Boc$_3$Arg Moiety Interacts Directly with the Proteasome.

Boc$_3$Arg-induced protein degradation is proteasome-dependent as clearly demonstrated by the observation that three different proteasome inhibitors block degradation. No signs of ubiquitylation were observed, even in the presence of deubiquitylating enzyme inhibitors. Therefore, we tentatively conclude that ubiquitylation is not required—tentatively because mammalian cells contain many deubiquitylating enzymes so complete inhibition cannot be assured.

Protcasome-dependent, ubiquitin-independent, protein degradation is more pervasive than generally realized. Oxidized protein degradation is probably the best characterized example of this phenomenon, though unstructured proteins also appear to be degraded by this route. Importantly, these pathways are not yet completely defined. Whereas ubiquitin-mediated degradation utilizes the 26S proteasome and is ATP-dependent, oxidized protein degradation requires only the core 20S proteasome and is ATP-independent. The 20S proteasome is a cylinder formed by 4 heptameric rings: two rings of β subunits form the proteolytic chamber at the center while two rings of α subunits are found on each end. The proteolytic chamber contains three kinds of active sites, one that cleaves at hydrophobic residues (the chymotrypsin-like sites), one that cleaves at positively charged residues (the trypsin-like sites) and one that cleaves at negatively charged residues (the caspase-like sites). The entrance to the proteolytic chamber is gated by N-terminal extensions of the α subunits. In the 26S proteasome, the 19S regulatory subunit caps the ends of the 20S cylinder, interacting with the α subunits to control access to the proteolytic chamber. The 19S regulatory subunit also interacts with ubiquitin chains, and uses ATP to unfold the ubiquitylated protein so that it can enter the proteasome. The gates are also regulated by the 11S activators, but in this case gate opening appears to be ATP-independent. The biological roles of the 11S activators are not understood. Intriguingly, hydrophobic peptides allosterically activate all three proteasome active sites, presumably by opening the gates, suggesting that unfolded proteins may enter in a similar manner. Perhaps $Boc_3Arg$ also interacts with these allosteric sites, opening the gates and allowing passage of the target protein into the proteolytic chamber.

Model 2: The $Boc_3Arg$ Moiety Interacts with the Target Protein, Making it Susceptible to Proteasomal Degradation.

Precedence for this mechanism can be found in the interactions of fulvestrant with the estrogen receptor. The preliminary results suggest that $Boc_3Arg$ interacts with eDHFR, as evidenced by the lower melting temperature. We hypothesize that the $Boc_3Arg$ intercalates into the protein, perturbing the structure and facilitating degradation.

Model 3: The $Boc_3Arg$ Moiety Interacts Directly with Another Cellular Factor that Mediates Degradation.

Potential factors include chaperones, 11S activators and ubiquitin ligases.

$Boc_3Arg$ May Act to Steer Proteins Directly into the Proteasome.

Model 1 proposes that the $Boc_3Arg$ moiety interacts with the 20S proteasome, opening the gates and causing degradation of the target protein. Several testable predictions arise from this model:

Sufficiency of 20S Proteasome Degradation.

Figure 18:
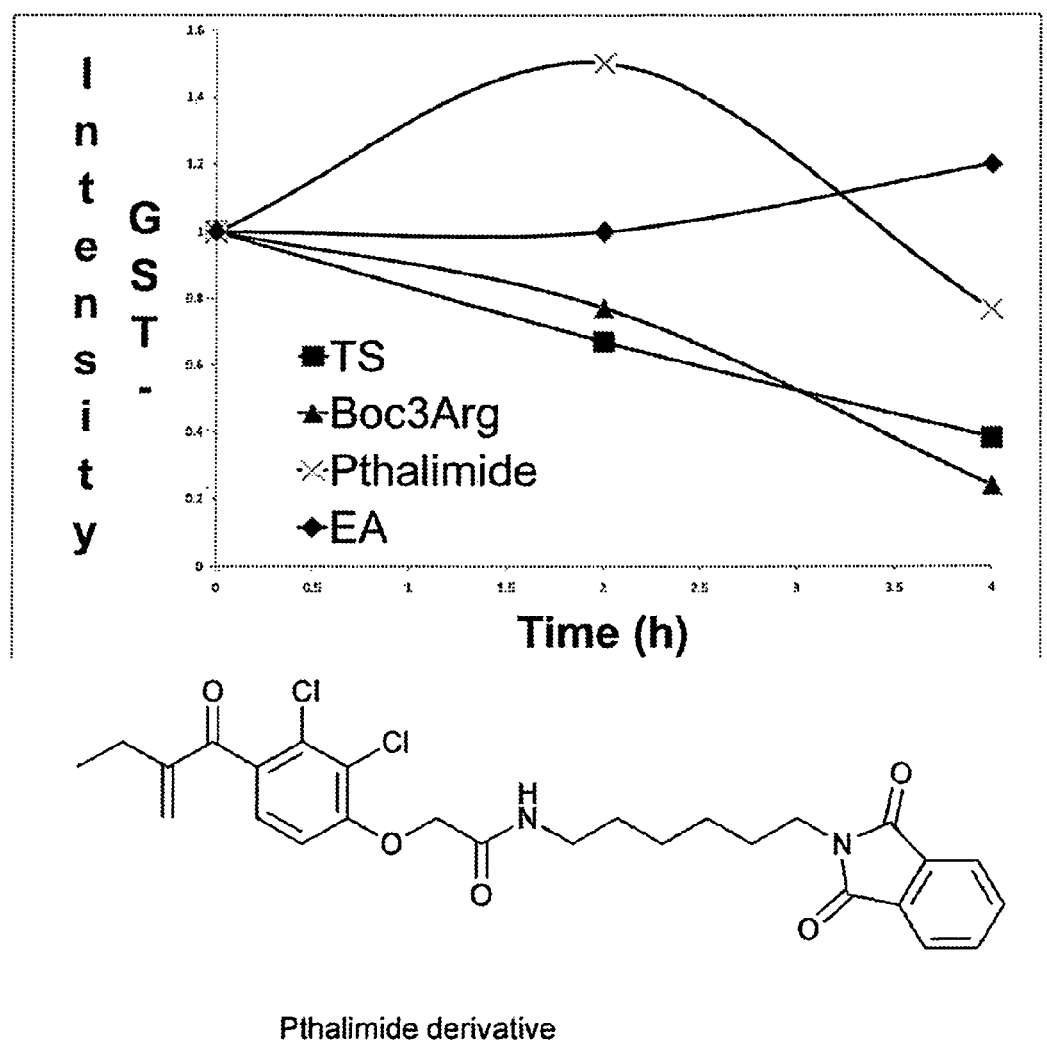
FIG. 18 depicts the degradation of GST-α-HA in HeLa cell lysates by various EA derivatives. EA=5, Ts=2, and Boc3Arg=1 as shown in FIG. 1. The structure of the phthalimide derivative is shown.

We will test this idea by characterizing the degradation EA-$Boc_3Arg$/GST by purified proteasomes obtained from commercial sources (BostonBiochem). Preliminary experiments indicate that the 20S proteasome degrades $Boc_3$-Arg modified proteins (FIG. 18). This degradation does not require the addition of ATP. Similar results are obtained with the 20S immunoproteasome, which contains three alternate β subunits (not shown). We will further characterize this reaction to determine if this activity is sufficiently robust to account for the degradation in lysates.

$Boc_3Arg$ May Act to Promote Gate Opening.

Hydrophobic peptides stimulates the 20S proteasome-catalyzed hydrolysis of peptide substrates for all three active sites by 6 to 90-fold. This allosteric activation displays strong positive cooperativity, with Hill coefficients of 4-17. If $Boc_3Arg$ also interacts with these allosteric sites, then a similar stimulation of peptide substrate hydrolysis should be observed, with similar positive cooperativity. We will monitor the effect of $Boc_3Arg$ on the 20S proteasome-catalyzed hydrolysis of Suc-Leu-Leu-Val-Tyr-AMC (substrate for chymotrypsin-like activity), Suc-Leu-Leu-Glu-AMC (substrate for caspase-like activity) and Boc-Leu-Arg-Arg-AMC (substrate for trypsin-like activity). These substrates are commercially available (BostonBiochem). If $Boc_3Arg$ opens the gate, then all the hydrolysis of all three substrates will be stimulated. We are well-aquatinted with these assays from our work on trypsin (e.g., (56)). Strong cooperativity should be observed if $Boc_3Arg$ activates the 20S proteasome in a manner similar to hydrophobic peptides.

We expect that these experiments will show that $Boc_3Arg$-induced degradation requires only the 20S proteasome. If the 20S proteasome is not sufficient, we will test the 26S proteasome because the 19S regulatory subunit has also been implicated in some ubiquitin-independent degradation. We will also determine if specific candidate factors are required. For example, the degradation of oxidized calmodulin requires the presence of Hsp90, so we will add Hsp90 to our experiments. The 11S regulatory subunit (aka PA28) has also been linked to ubiquitin-independent degradation, so this is another likely candidate. Lastly, we will perform some additional experiments to confirm the ubiquitin-independence of $Boc_3Arg$-induced degradation. For example, thermosensitive Ube1 cells can be used to disable ubiquitin-dependent protein degradation; we will test the effectiveness of $Boc_3Arg$-induced degradation in these cells.

We further expect that the experiments above will show that $Boc_3Arg$ promotes the opening of the gates, and that the SAR of this activity will match the SAR for degradation. This outcome would give us a facile assay for the discovery of additional destabilizing moieties. If this proves not to be the case, then we will explore the possibility that $Boc_3Arg$ simply binds to the proteasome. Localization of proteins to the proteasome is sufficient to induce degradation, so this is a viable alternative. In this case, we expect that $Boc_3Arg$ will compete with $Boc_3Arg$-modified proteins, but not with peptides such as Suc-Leu-Leu-Glu-AMC.

$Boc_3Arg$—DHFR Interaction.

The working hypothesis for Model 2 is that the $Boc_3Arg$ group intercalates into protein structure, exposing a hydrophobic surface that promotes degradation. We will use NMR spectroscopy to determine which regions of eDHFR interact with $Boc_3Arg$-TMP. These experiments will exploit knowledge gleaned from decades of NMR investigations of eDHFR structure. Sequential assignments are already in hand for apoenzyme and many inhibitor complexes. Backbone perturbations can be readily identified with $^1H$, $^{15}N$-HSQC experiments of $^{15}N$-labeled protein; spectra of apoenzyme, DFHR.TMP and DHFR.TMP-$Boc_3Arg$ complexes will be compared to understand how the $Boc_3Arg$ moiety interacts with the protein. NADPH increases the affinity of TMP, so we will also examine the DFHR.TMP.NADPH and DHFR.TMP-$Boc_3Arg$.NADPH complexes. If Boc3Arg interacts with eDHFR, then the spectrum of these complexes will differ markedly from the TMP complexes.

If $Boc_3Arg$ intercalates into the protein as proposed, then the structural perturbation will most likely extend well beyond the residues that actually contact the $Boc_3Arg$ moiety. Therefore we will also produce $^{13}C$-labeled protein for $^{12}C$, $^{13}C$-NOE experiments. The use of double-half filters will enable the identification of the residues that interact directly with $Boc_3Arg$.

If no interaction is observed, then Model 2 can be eliminated. If an interaction is observed, and the SAR matches that of the overall degradation established in Aim 1, then Model 2 is likely to be valid.

Other Factors are Involved in $Boc_3Arg$-Induced Degradation.

These experiments may be pursued if the above experiments suggest that other factors are involved in $Boc_3Arg$-induced degradation.

Proteins that Interact with $Boc_3Arg$.

We will construct a $Boc_3Arg$ affinity resin by attaching the $Boc_3Arg$-linker-amine to an activated resin such as Toyopearl AF-Tresyl-650M. We will use an inactive compound such as butyryl-linker amine to construct a resin for a negative control. We will identify proteins in Hela cell lysates that bind to the Boc3Arg resin but not to the control resin using a commercially mass spectrometry facility.

Factors that Promote $Boc_3Arg$-Induced Degradation In Vitro.

We will add fractions of Hela lysates to purified proteasome to identify factors that promote degradation using traditional protein purification methods.

INCORPORATION BY REFERENCE

All publications and patents mentioned herein are hereby incorporated by reference in their entirety as if each individual publication or patent was specifically and individually indicated to be incorporated by reference. The following patents/applications are also incorporated by reference in their entireties: U.S. Pat. No. 5,122,463, U.S. Pat. No. 5,766,927, U.S. Pat. No. 5,851,791, U.S. Pat. No. 5,866,121, U.S. Pat. No. 6,222,095, U.S. Pat. No. 6,670,348, U.S. Pat. No. 6,217,864, U.S. Pat. No. 6,306,663, U.S. Pat. No. 6,559,280, US 20040102458A1, EP 01426055A1 and US 20050152888A1 In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

We claim:

1. A compound, comprising:
   a protein-binding moiety which binds a protein,
   a tag which promotes the degradation of said protein, and
   a covalent linker which connects the protein-binding moiety to the tag;
   wherein
   the protein binding moiety is selected from the group consisting of

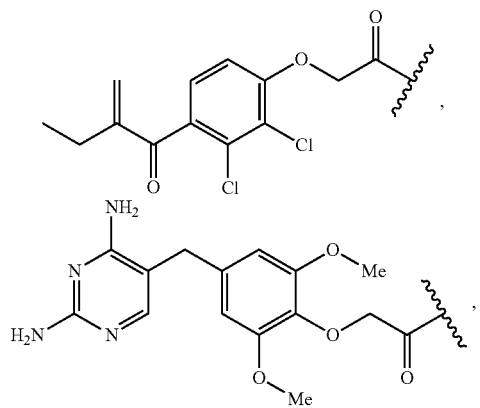

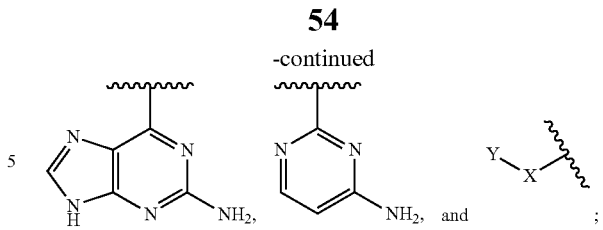

X is —$(CH_2)_n$—;
Y is chloro, bromo, or iodo;
the covalent linker is —N(H)$[CH_2]_n$N(H)—, —$(OCH_2CH_2)_n$O—, or —$(OCH_2CH_2)_n$NH—;
n is independently 1-10 inclusive;
the tag is

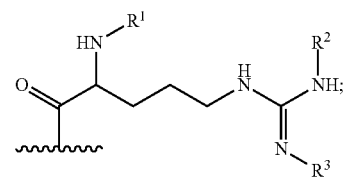

$R^1$, $R^2$, and $R^3$ are tert-butoxycarbonyl.

2. The compound of claim 1, wherein the protein is selected from the group consisting of glutathione-S-transferase α1 (GST), dihydrofolate reductase (DHFR), botulinum toxin (BoNT), Bcr-Abl, thioredoxin interacting protein (TXNIP), mutant forms of Ras that cause cancer, and mutant forms of IMP dehydrogenase type 1 (IMPDH1) that cause retinitis pigmentosa.

3. The compound of claim 1, wherein the protein is a fusion protein comprising a first protein and a second protein; the protein-binding moiety binds the first protein; and the tag promotes the degradation of the second protein.

4. The compound of claim 3, wherein the first protein is GST, DHFR, SNAP, CLIP, or HALO.

5. The compound of claim 1, wherein the compound is represented by formula I, or a pharmaceutically acceptable salt thereof,

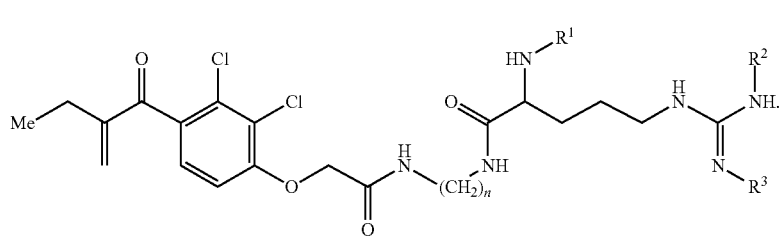

6. The compound of claim 1, wherein the compound is represented by formula II, or a pharmaceutically acceptable salt thereof, 7. A compound represented by formula III, or a pharmaceutically acceptable salt thereof, wherein X is —(CH$_2$)$_n$—;
n is 1-10 inclusive;
R$^1$, R$^2$, and R$^3$ are tert-butoxycarbonyl.

8. The compound of claim 1, wherein the compound is represented by formula IV, or a pharmaceutically acceptable salt thereof, 9. A compound represented by formula VI, or a pharmaceutically acceptable salt thereof, wherein X is —(CH$_2$)$_n$—;
n is 1-10 inclusive;
R$^1$, R$^2$, and R$^3$ are tert-butoxycarbonyl.

10. A composition, comprising a compound of claim 1; and a pharmaceutically acceptable excipient.

11. A compound-represented by formula IIa, or a pharmaceutically acceptable salt thereof, wherein
X is —N(H)[CH$_2$]$_n$N(H)—;
n is 1-10;
R$^1$ is tert-butoxycarbonyl;
R$^2$ is tert-butoxycarbonyl, or p-toluenesulfonyl; and
R$^3$ is tert-butoxycarbonyl or hydrogen.

12. A composition, comprising a compound of claim 11; and a pharmaceutically acceptable excipient.

* * * * *